United States Patent
Stauss et al.

(10) Patent No.: US 12,077,774 B2
(45) Date of Patent: Sep. 3, 2024

(54) METHOD FOR ENHANCING THE SUPPRESSIVE PROPERTIES OF TREG CELLS

(71) Applicant: UCL Business Ltd., London (GB)

(72) Inventors: Hans Stauss, London (GB); Jenny L. McGovern, London (GB)

(73) Assignee: UCL Business Ltd., London (GB)

( * ) Notice: Subject to any disclaimer, the term of this patent is extended or adjusted under 35 U.S.C. 154(b) by 964 days.

(21) Appl. No.: 17/048,239

(22) PCT Filed: Apr. 17, 2019

(86) PCT No.: PCT/GB2019/051098
§ 371 (c)(1),
(2) Date: Oct. 16, 2020

(87) PCT Pub. No.: WO2019/202323
PCT Pub. Date: Oct. 24, 2019

(65) Prior Publication Data
US 2021/0079425 A1 Mar. 18, 2021

(30) Foreign Application Priority Data
Apr. 18, 2018 (GB) ..................... 1806330
Apr. 18, 2018 (GB) ..................... 1806331

(51) Int. Cl.
| | | |
|---|---|---|
| C12N 15/87 | (2006.01) | |
| A61K 35/12 | (2015.01) | |
| A61K 35/17 | (2015.01) | |
| A61K 38/00 | (2006.01) | |
| C07K 14/725 | (2006.01) | |
| C07K 14/74 | (2006.01) | |
| C12N 5/0783 | (2010.01) | |

(52) U.S. Cl.
CPC .......... *C12N 15/87* (2013.01); *A61K 35/17* (2013.01); *C07K 14/7051* (2013.01); *C07K 14/70539* (2013.01); *C12N 5/0637* (2013.01); *A61K 2035/122* (2013.01); *A61K 38/00* (2013.01); *C12N 2510/00* (2013.01)

(58) Field of Classification Search
None
See application file for complete search history.

(56) References Cited

U.S. PATENT DOCUMENTS

| | | |
|---|---|---|
| 7,131,958 B2 | 11/2006 | Deverre |
| 7,147,626 B2 | 12/2006 | Goodman et al. |
| 2009/0010885 A1 | 1/2009 | Vandenbark et al. |
| 2009/0285795 A1 | 11/2009 | Patell |
| 2014/0004133 A1 | 1/2014 | Bykovskaia et al. |
| 2019/0290691 A1 | 9/2019 | Jäckel et al. |
| 2020/0330515 A1* | 10/2020 | Maus .............. C12N 5/0637 |
| 2023/0226182 A1 | 7/2023 | Stauss et al. |

FOREIGN PATENT DOCUMENTS

| | | |
|---|---|---|
| CN | 103212064 A | 7/2013 |
| EP | 0669836 | 7/1996 |
| EP | 1633398 | 3/2006 |
| EP | 2000149 | 12/2008 |
| EP | 3243838 | 11/2017 |
| EP | 3263595 | 1/2018 |
| GB | 2611498 B | 7/2023 |
| WO | 9941397 | 8/1999 |
| WO | 0009693 A2 | 2/2000 |
| WO | 0179518 | 10/2001 |
| WO | 02090600 A2 | 11/2002 |
| WO | 2005000898 | 1/2005 |
| WO | 2008095141 A2 | 8/2008 |
| WO | WO-2009/050283 A1 | 4/2009 |
| WO | 201315339 | 1/2013 |
| WO | WO-2014/145970 A1 | 9/2014 |
| WO | WO-2014/183056 A1 | 11/2014 |
| WO | 2015092362 A1 | 6/2015 |
| WO | 2016100241 | 6/2016 |
| WO | 2017058752 | 4/2017 |
| WO | WO-2017/062035 A1 | 4/2017 |
| WO | 2018001874 A1 | 1/2018 |
| WO | 2018002358 | 1/2018 |
| WO | 2018231759 | 12/2018 |
| WO | 2018236909 | 12/2018 |
| WO | 2019079034 A1 | 4/2019 |
| WO | 2019202323 | 10/2019 |
| WO | 2019241549 | 12/2019 |
| WO | 2020044055 | 3/2020 |
| WO | 2020201230 | 10/2020 |

(Continued)

OTHER PUBLICATIONS

Polypeptide [Internet]. Bethesda (MD): National Library of Medicine (US), National Center for Biotechnology Information; [2023] —Accession No. NP_054728, Forkhead box protein P3 isoform a [*Homo sapiens*]. Available from: https://www.ncbi.nlm.nih.gov/protein/NP_054728.2. (Year: 2023).*
Intention to Grant issued for Application No. GB2300872.5, dated Apr. 19, 2023. 2 pages.
Notification of Grant issued for Application No. GB2300872.5, dated Jun. 20, 2023. 2 pages.
Examination Report issued for Application No. GB2018103.8, dated Jan. 10, 2023, 4 pages.
Peng et al. "The effect of foxp3-overexpressing Treg cells on non-small cell lung cancer cells", Molecular Medicine Reports, 17: 5860-5868, 2018.
Abbas, Abul K., et al. "Regulatory T cells: recommendations to simplify the nomenclature." Nature immunology 14.4 (2013): 307-308.
Allen, Elizabeth S., et al. "Improved accuracy of clinical HLA genotyping by next-generation DNA sequencing affects unrelated donor search results for hematopoietic stem cell transplantation." Human immunology 79.12 (2018): 848-854.

(Continued)

*Primary Examiner* — Allison M Fox
*Assistant Examiner* — Alyssa G Weston
(74) *Attorney, Agent, or Firm* — Meunier Carlin & Curfman LLC

(57) ABSTRACT

The present invention relates to a method for enhancing the ability of regulatory T cells (Tregs) to suppress immune responses comprising increasing FOXP3 expression in a population of Tregs.

10 Claims, 13 Drawing Sheets

Specification includes a Sequence Listing.

(56) References Cited

FOREIGN PATENT DOCUMENTS

| WO | 2020237045 A1 | 11/2020 |
|---|---|---|
| WO | 2021239812 | 12/2021 |

OTHER PUBLICATIONS

Brentjens, Renier J., et al. "Genetically targeted T cells eradicate systemic acute lymphoblastic leukemia xenografts." Clinical cancer research 13.18 (2007): 5426-5435.
Budde, Lihua E., et al. "Combining a CD20 chimeric antigen receptor and an inducible caspase 9 suicide switch to improve the efficacy and safety of T cell adoptive immunotherapy for lymphoma." PloS one 8.12 (2013): e82742.
Casucci, Monica, et al. "CD44v6-targeted T cells mediate potent antitumor effects against acute myeloid leukemia and multiple myeloma." Blood, The Journal of the American Society of Hematology 122.20 (2013): 3461-3472.
Casucci, Monica, and Bondanza, Attilio. "Suicide gene therapy to increase the safety of chimeric antigen receptor-redirected T lymphocytes." Journal of Cancer 2 (2011): 378.
Chen, Xiaoying, et al. "Fusion protein linkers: property, design and functionality." Advanced drug delivery reviews 65.10 (2013): 1357-1369.
Choo, Sung Yoon. "The HLA system: genetics, immunology, clinical testing, and clinical implications." Yonsei medical journal 48.1 (2007): 11-23.
Choudhary, Narendra S., et al. "Acute and chronic rejection after liver transplantation: what a clinician needs to know." Journal of clinical and experimental hepatology 7.4 (2017): 358-366.
Coffin et al., 1997, "Retroviruses", Cold Spring Harbour Laboratory Press Eds: JM Coffin, SM Hughes, HE Varmus pp. 758-763.
Di Stasi, Antonio, Salvado, et al. "T lymphocytes coexpressing CCR4 and a chimeric antigen receptor targeting CD30 have improved homing and antitumor activity in a Hodgkin tumor model." Blood, The Journal of the American Society of Hematology 113.25 (2009): 6392-6402.
Donnelly, Michelle LL, et al. "The 'cleavage' activities of foot-and-mouth disease virus 2A site-directed mutants and naturally occurring '2A-like'sequences." Journal of General Virology 82.5 (2001): 1027-1041.
Fan, Chia-Yu, et al. "De novo protein sequencing, humanization and in vitro effects of an antihuman CD34 mouse monoclonal antibody." Biochemistry and biophysics reports 9 (2017): 51-60.
Guedan, Sonia, et al. "Engineering and design of chimeric antigen receptors." Molecular Therapy-Methods & Clinical Development 12 (2019): 145-156.
Haque, Mohammad, et al. "Development of stem cell-derived antigen-specific regulatory T cells against autoimmunity." JoVE (Journal of Visualized Experiments) 117 (2016): e54720.
Hiroe, Ayaka, et al. "Rearrangement of gene order in the phaCAB operon leads to effective production of ultrahigh-molecular-weight poly [(R)-3-hydroxybutyrate] in genetically engineered *Escherichia coli*." Applied and environmental microbiology 78.9 (2012): 3177-3184.
Holzinger, Astrid, and Abken, Hinrich. "CAR T cells: a snapshot on the growing options to design a CAR." HemaSphere 3.1 (2019).
Imai, et al. "Chimeric receptors with 4-1BB signaling capacity provoke potent cytotoxicity against acute lymphoblastic leukemia." Leukemia 18.4 (2004): 676-684.
Klein, Joshua S., et al. "Design and characterization of structured protein linkers with differing flexibilities." Protein Engineering, Design & Selection 27.10 (2014): 325-330.
Li, Meng, et al. "Mimotope vaccination for epitope-specific induction of anti-CD20 antibodies." Cellular immunology 239.2 (2006): 136-143.
Lin, Yuan, et al. "An effective way of producing fully assembled antibody in transgenic tobacco plants by linking heavy and light chains via a self-cleaving 2A peptide." Frontiers in Plant Science 9 (2018): 1379.

Liu, Weihong, et al. "CD127 expression inversely correlates with FoxP3 and suppressive function of human CD4+ T reg cells." The Journal of experimental medicine 203.7 (2006): 1701-1711.
Liu, Ziqing, et al. "Systematic comparison of 2A peptides for cloning multi-genes in a polycistronic vector." Scientific reports 7.1 (2017): 1-9; 2193.
Lopes, Jared E., et al. "Analysis of FOXP3 reveals multiple domains required for its function as a transcriptional repressor." The Journal of Immunology 177.5 (2006): 3133-3142.
Lozano, Teresa, et al. "Searching for the Achilles Heel of FOXP3." Frontiers in oncology 3 (2013): 294.
Macdonald, et al. "Methods to manufacture regulatory T cells for cell therapy", Clinical and Experimental Immunology, Apr. 15, 2019, XP055772005, GB, p. 54, col. 1, lines 54-57.
Maher, John, et al. "Human T-lymphocyte cytotoxicity and proliferation directed by a single chimeric TCRY/CD28 receptor." Nature biotechnology 20.1 (2002): 70-75.
Merten, O-W. "State-of-the-art of the production of retroviral vectors." The Journal of Gene Medicine: A cross-disciplinary journal for research on the science of gene transfer and its clinical applications 6.S1 (2004): S105-S124.
Merten, Otto-Wilhelm, et al. "Production of lentiviral vectors." Molecular Therapy-Methods & Clinical Development 3 (2016): 16017.
Milone, Michael C., et al. "Chimeric receptors containing CD137 signal transduction domains mediate enhanced survival of T cells and increased antileukemic efficacy in vivo." Molecular therapy 17.8 (2009): 1453-1464.
Mohseni, Yasmin R., et al. "The future of regulatory T cell therapy: promises and challenges of implementing CAR technology." Frontiers in immunology 11 (2020): 1608.
Nicaise, Magali, et al. "Affinity transfer by CDR grafting on a nonimmunoglobulin scaffold." Protein Science 13.7 (2004): 1882-1891.
Noyan et al. "Prevention of Allograft Rejection by Use of Regulatory T Cells With an MHC-Specific Chimeric Antigen Receptor", American Journal of Transplantation, vol. 17, No. 4, Feb. 6, 2017, pp. 917-930, XP055401666, DK.
Perkey, Eric, and Maillard, Ivan. "New insights into graft-versus-host disease and graft rejection." Annual Review of Pathology: Mechanisms of Disease 13 (2018): 219-245.
Perosa, Federico, et al. "Identification of an antigenic and immunogenic motif expressed by two 7-mer rituximab-specific cyclic peptide mimotopes: implication for peptide-based active immunotherapy." The Journal of Immunology 179.11 (2007): 7967-7974.
Polansky, Julia K., et al. "DNA methylation controls Foxp3 gene expression." European journal of immunology 38.6 (2008): 1654-1663.
Pulè, Martin A., et al. "A chimeric T cell antigen receptor that augments cytokine release and supports clonal expansion of primary human T cells." Molecular Therapy 12.5 (2005): 933-941.
Qian, Zhaohui, et al. "Engineered regulatory T cells coexpressing MHC class II: peptide complexes are efficient inhibitors of autoimmune T cell function and prevent the development of autoimmune arthritis." The Journal of Immunology 190.11 (2013): 5382-5391.
Raffin, Caroline, et al. "Treg cell-based therapies: challenges and perspectives." Nature Reviews Immunology 20.3 (2020): 158-172.
Reddy Chichili, Vishnu Priyanka, et al. "Linkers in the structural biology of protein-protein interactions." Protein science 22.2 (2013): 153-167.
Roberts, Darren M., et al. "The treatment of acute antibody-mediated rejection in kidney transplant recipients—a systematic review." Transplantation 94.8 (2012): 775-783.
Sack, Brandon K., et al. "Development of gene transfer for induction of antigen- specific tolerance." Molecular Therapy—Methods & Clinical Development 1 (2014): 14013.
Sicard, et al. "Engineering therapeutic T cells to suppress alloimmune responses using TCRs, CARs, or BARs", American Journal of Transplantation, vol. 18, No. 6, Jun. 1, 2018, pp. 1305-1311, XP055771999, DK.

(56) References Cited

OTHER PUBLICATIONS

Sheldon, Stephen, and Poulton, Kay. "HLA typing and its influence on organ transplantation." Transplantation Immunology (2006): 157-174.
Song, Xiaomin, et al. "Structural and biological features of FOXP3 dimerization relevant to regulatory T cell function." Cell reports 1.6 (2012): 665-675.
Stavrou, Maria. CAR Gene Transfer to Generate Antigen Specific Regulators. Diss. UCL (University College London), 2016. 248 pages.
Tenspolde, Michel, et al. "Regulatory T cells engineered with a novel insulin-specific chimeric antigen receptor as a candidate immunotherapy for type 1 diabetes." Journal of Autoimmunity 103 (2019): 102289.
Van Rosmalen, Martijn, et al. "Tuning the flexibility of glycine-serine linkers to allow rational design of multidomain proteins." Biochemistry 56.50 (2017): 6565-6574.
Vaughan, Cara K., and Sollazzo, Maurizio. "Of minibody, camel and bacteriophage." Combinatorial Chemistry & High Throughput Screening 4.5 (2001): 417-430.
Wang, Bo, et al. "Structural comparison of two anti-CD20 monoclonal antibody drug products using middle-down mass spectrometry." Analyst 138.10 (2013): 3058-3065.
Watkins, N. A., et al. "The isolation and characterisation of human monoclonal HLA-A2 antibodies from an immune V gene phage display library." Tissue Antigens 55.3 (2000): 219-228.
Watkins, N. A., et al. "Molecular studies of anti-HLA-A2 using light-chain shuffling: a structural model for HLA antibody binding." Tissue Antigens 63.4 (2004): 345-354.
Ziegler, Steven F. "FOXP3: of mice and men." Annual review of immunology 24.1 (2006): 209-226.
Zufferey, R., 2002. Production of lentiviral vectors. In Lentiviral Vectors (pp. 107-121). Springer, Berlin, Heidelberg.
International Search Report and Written Opinion issued for Application No. PCT/EP2021/073714, dated Jan. 5, 2022. 21 pages.
International Search Report and Opinion in Application No. PCT/GB2020/052695, mailed Feb. 18, 2021, 17 pages.
Search Report issued for Application No. GB2013477.1, dated Feb. 25, 2021.
Search report issued for Application No. GB2016862.1, dated Apr. 23, 2021, 6 pages.
Communication pursuant to Article 94(3) EPC for EP Application No. 19719600.9 dated Jun. 6, 2023.
English translation of Office Action for Chinese Application No. 201980026673.5 dated May 19, 2023.
Office Action issued in Chinese Patent No. 201980026673.5 issued on May 19, 2023.
Jenny L. McGovern et al., "Engineering Specificity and Function of Therapeutic Regulatory T Cells, " Frontiers in Immunology, vol. 8. Nov. 10, 2017.
He Yunfeng et al., "Foxp3 expression retroviral vector reinforces the function of Treg cell," Immunological Journal, vol. 31. No 11. Nov. 2015.
Office Action Issued in Japanese Application No. 2020-556883, dated Feb. 21, 2023, 6 pages.
Combined Search and Examination Report issued for Application GB2300916.0, dated Feb. 2, 2023, 5 pages.
Schmetterer et al., Bet v 1-specific T cell receptor/forkhead box protein 3 transgenic T cells suppress Bet v 1-speciifc T cell effector function in an activation-dependent manner. J Allergy Clin Immunol 2011. 127: 238-245.
Written Opinion issued for Singaporean Application No. 11202018154U by Intellectual Property Office of Singapore, dated Jun. 26, 2022. 7 pages.

Office Actionis sued for Application No. GB2018103.8, dated Nov. 24, 2022, 5 pages.
Maria Stavrou, Car Gene Transfer to Generate Antigen Specific Regulators, A thesis submitted to University College London for the degree of Doctor of Philosophy, 2016, 248 pages, London England.
Adair et al., Human Tregs Made Antigen Specific by Gene Modification: The Power to Treat Autoimmunity and Antidrug Antibodies with Precision, Front. Immunol., 8:1117 (Sep. 2017).
Dawson et al., Engineered Tolerance: Tailoring Development, Function, and Antigen-Specificity of Regulatory T Cells, Front Immunol., 8:1460 (Nov. 2017).
Fransson et al., CAR/FoxP3-engineered T regulatory cells target the CNS and suppress EAE upon intranasal delivery, J. Neuroinflammation, 9:112 (May 2012).
Great Britain Patent Application No. GB1806330.5, Search Report, dated Dec. 18, 2018.
International Application No. PCT/GB2019/051098, International Search Report and Written Opinion, mailed Jun. 18, 2019.
Mekala et al., IL-10-dependent infectious tolerance after the treatment of experimental allergic encephalomyelitis with redirected CD4+CD25+ T lymphocytes, Proc. Natl. Acad. Sci. USA, 102(33):11817-22 (Aug. 2005).
Muraro et al., Immunodominance of a low-affinity major histocompatibility complex-binding myelin basic protein epitope (residues 111-129) in HLA-DR4 (B1*0401) subjects is associated with a restricted T cell receptor repertoire, J. Clin. Invest., 100(2):339-49 (Jul. 1997).
Peng et al., The effect of foxp3-overexpressing Treg cells on non-small cell lung cancer cells, Mol. Med. Reports, 17(4):5860-5868 (Apr. 2018).
Stephens et al., Curing CNS autoimmune disease with myelin-reactive Foxp3+ Treg, Eur. J. Immunol., 39(4):1108-17 (Apr. 2009).
Tuohy et al., Preemptive targeting of the epitope spreading cascade with genetically modified regulatory T cells induces Tr1 immune deviation during EAE, FASEB Journal, 15(5):A1212 (Mar. 2001).
Wright et al., Adoptive therapy with redirected primary regulatory T cells results in antigen-specific suppression of arthritis, Proc. Natl. Acad. Sci. USA, 106(45):19078-83 (Nov. 2009).
Bank et al., Inhibition of alanyl-aminopeptidase on CD4+CD25+ regulatory T-cells enhances expression of FoxP3 and TGF-beta1 and ameliorates acute colitis in mice, 20(4):483-92 (Oct. 2007).
Great Britain Patent Application No. GB1806331.3, Search Report, dated Dec. 21, 2018.
Huang et al., Histone/protein deacetylase 11 targeting promotes Foxp3+Treg function, Scientific Reports, 7:8626 (Aug. 2017).
Lu et al., Rapamycin regulates iTreg function through CD39 and Runx1 pathways, J. Immunol. Res., vol. 2014, Article ID 989434 (Mar. 2014).
Singh et al., Concomitant analysis of Helios and Neuropilin-1 as a marker to detect thymic derived regulatory T cells in naive mice, Scientific Reports, 5:7767 (Jan. 2015).
Zhao et al., Growth arrest-specific 6 enhances the suppressive function of CD4+CD25+ regulatory T cells mailing through Axl receptor, Mediators of Inflammation, vol. 2017, Article ID 6848430 (2017).
Combined Search and Examination Report issued for Application GB2300872.5, dated Jan. 31, 2023, 6 pages.
Second Office Action issued in CN Application No. 201980026673.5 dated Nov. 29, 2023.
Liu et al., Blood Purification Therapeutics in Critical and Emergency Diseases, Edited by Zhangsuo LIU et al., Henan Science and Technology Press, 2017.
Examination Report issued for Application GB2016862.1, dated Sep. 22, 2023, 7 pages.
Communication pursuant to Article 94(3) EPC for EP Application No. 19719600.9 dated Aug. 22, 2023.

\* cited by examiner

METHOD FOR ENHANCING THE SUPPRESSIVE PROPERTIES OF TREG CELLS

CROSS REFERENCE TO RELATED APPLICATIONS

This application is a U.S. National Stage of International Application No. PCT/GB2019/051098, filed on Apr. 17, 2019, which claims priority benefit under § 119 of United Kingdom Patent Application No. 1806331.3, filed on Apr. 18, 2018, and United Kingdom Patent Application No. 1806330.5, filed on Apr. 18, 2018.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "55268_Seqlisting.txt." The Sequence Listing was created on Sep. 21, 2020, and is 20,030 bytes in size. The subject matter of the Sequence Listing is incorporated herein in its entirety by reference.

FIELD OF THE INVENTION

The present invention relates to a method for enhancing the ability of regulatory T cells (Tregs) to suppress immune responses. In particular, the present invention relates to a method of increasing FOXP3 expression in Tregs. The present invention further relates to an engineered Treg provided by the method of the invention and to methods and uses of such an engineered Treg.

BACKGROUND TO THE INVENTION

Regulatory T cells (Tregs) are a type of T cell that modulates the activity of the immune system. Generally, Tregs are immunosuppressive, down-regulating immune responses to stimuli. In particular, Tregs suppress induction and proliferation of conventional T cells, some types of which are directly involved in immune responses (e.g. cytotoxic T cells). The suppressive effect of Tregs can be directed towards specific antigens by expression of recombinant T cell receptor (TCR) constructs that recognise peptides matching epitopes found within the antigen in question. Similarly, the suppressive effect of Tregs can be directed towards specific targets by expression of chimeric antigen receptors (CARs) that recognise antigens expressed on the surface of target cells. Conventional T cells can be differentiated towards a regulatory phenotype ex-vivo by expressing FOXP3 in said cells.

In autoimmune and inflammatory central nervous system (CNS) diseases, the immune system attacks self-antigens. For example, in Multiple Sclerosis (MS), the most common neurological disorder among young adults, the immune system attacks the myelin sheath of neurons of the central nervous system.

Current treatments for autoimmune and inflammatory CNS diseases generally suppress the immune system. For example, one treatment includes transplantation of bone marrow along with administration of cytostatics and immunosupressive drugs. Autologous haematopoietic stem cell transplantation can have lasting beneficial effects for some subjects, but the procedure requires aggressive myelo-ablative conditioning which is associated with substantial toxicity and risk.

Although several disease-modifying treatments (DMTs) have been approved to reduce the frequency of clinical relapses, most patients continue to clinically deteriorate under current therapy schedules. Neither DMTs nor stem cell transplantation can mediate CNS-specific suppression of the immunopathology of autoimmune and inflammatory CNS diseases.

Currently, effective treatments for autoimmune and inflammatory CNS diseases do not exist. Treatment is focused on merely reducing its symptoms, usually by general suppression of the immune system. There is a need for a therapy which specifically targets local immune responses associated with onset and progression of CNS disease.

SUMMARY OF THE INVENTION

The present inventors have surprisingly found that exogenous FOXP3 expression in regulatory T cell (Tregs) (which already express endogenous FOXP3) enhances their regulatory function.

Accordingly, the invention provides a method for enhancing the ability of regulatory T cells (Tregs) to suppress immune responses.

The Tregs of the present invention are natural Tregs or induced Tregs which developed from conventional T cells. For example, the Tregs of the present invention are natural Tregs or induced Tregs which developed from conventional T cells in vivo. Suitable Treg cells include thymus-derived, natural Treg (nTreg) cells and peripherally generated, induced Treg (iTreg) cells. In other words, the Tregs of the present invention express endogenous FOXP3. Surprisingly, the present inventors have determined that increasing FOXP3 expression in Tregs which already express endogenous FOXP3 (e.g. by introducing exogenous FOXP3) enhances the regulatory function of the Tregs to a greater degree than the regulatory function provided by expressing exogenous FOXP3 in conventional T cells which do not express endogenous FOXP3.

The present inventors have further determined that increasing FOXP3 expression in Tregs which already express endogenous FOXP3 enables improved retention of a Treg functional profile in vivo following administration to a subject. For example, it has been determined that natural Tregs which do not express exogenous FOXP3 may lose their Treg profile following administration to a subject—for example natural Tregs which do not express exogenous FOXP may have reduced levels of FOXP3 expression and be capable of producing pro-inflammatory, effector cytokines after a period following administration to a subject. Tregs provided by the present invention may retain FOXP3 expression and have reduced capability to produce pro-inflammatory, effector cytokines after a period following administration to a subject.

In a preferred embodiment, the Tregs of the present invention are natural Tregs.

In one aspect, the invention provides a method for generating a population of regulatory T cells (Tregs) comprising providing a first population of Tregs and increasing FOXP3 expression in the first population of Tregs to generate a second population of Tregs.

The invention provides a method for enhancing the ability of a Tregs to suppress immune responses comprising increasing FOXP3 expression in the Treg.

In some embodiments of the invention, FOXP3 expression is increased by introducing into the Tregs a polynucleotide encoding a FOXP3 protein.

In some embodiments of the invention, the method for enhancing the ability of regulatory T cells (Tregs) to suppress immune responses comprises:

(a) isolating a Treg from a cell population; and
(b) increasing FOXP3 expression in Tregs.

Suitably, the Treg may refer to a population of Tregs (i.e. a plurality of Tregs).

The invention also provides an engineered Treg obtainable or obtained by the method of the invention.

The invention also provides an engineered Treg having higher FOXP3 expression than a non-engineered Treg.

In some embodiments the engineered Treg comprises an exogenous polynucleotide encoding a FOXP3 protein.

The invention also provides a pharmaceutical composition comprising an engineered Treg of the invention.

The invention also provides an engineered Treg of the invention or a pharmaceutical composition of the invention for use in prevention and/or treatment of a disease.

The invention also provides the use of an engineered Treg of the invention in the manufacture of a medicament.

The invention also provides a method for prevention and/or treatment of a disease comprising administering to a subject an engineered Treg or a composition of the invention.

Thy1.1+CD4+CD25+ Treg were isolated from lymph nodes and splenocytes of HLA-DRB*0401 transgenic mice by bead sort. Treg were transduced TCR, TCR+murine FOXP3 or cultured with virus-free supernatant (mock). 1 day after transduction TCR or TCR+FOXP3 transduced cells were injected into HLA-DRB*0401 transgenic hosts conditioned with 4Gy irradiation. 7 weeks later flow cytometry was used to determine the engraftment of transduced Treg A. Transduction efficiency was determined through expression of human variable 2.1 and murine Foxp3 on d1 post-transduction B. Splenocytes from mice that received Treg transduced with TCR or TCR+FOXP3 were stained with Thy1.1 to identify transferred cells (top panel) and FOXP3 and TCR (bottom panel) C. Cumulative data showing fold change in transduction efficiency (left panel) and fold change in absolute number of transduced cells (right panel) relative to day of injection for Treg transduced with TCR or TCR+FOXP3 (n=3). Error bars show standard error of the mean. Statistical analysis by unpaired t test D. Representative expression of FOXP3 within transduced cells 7 weeks after transfer. Graphs show cumulative of percentage FOXP3+ cells within the transduced population at week 7 (left) and the fold change in FOXP3+ cells relative to the day of injection (n=3). Error bars show standard error of the mean. *p=>0.05, **p=>0.01 determined by unpaired t test.

Figure 10A:
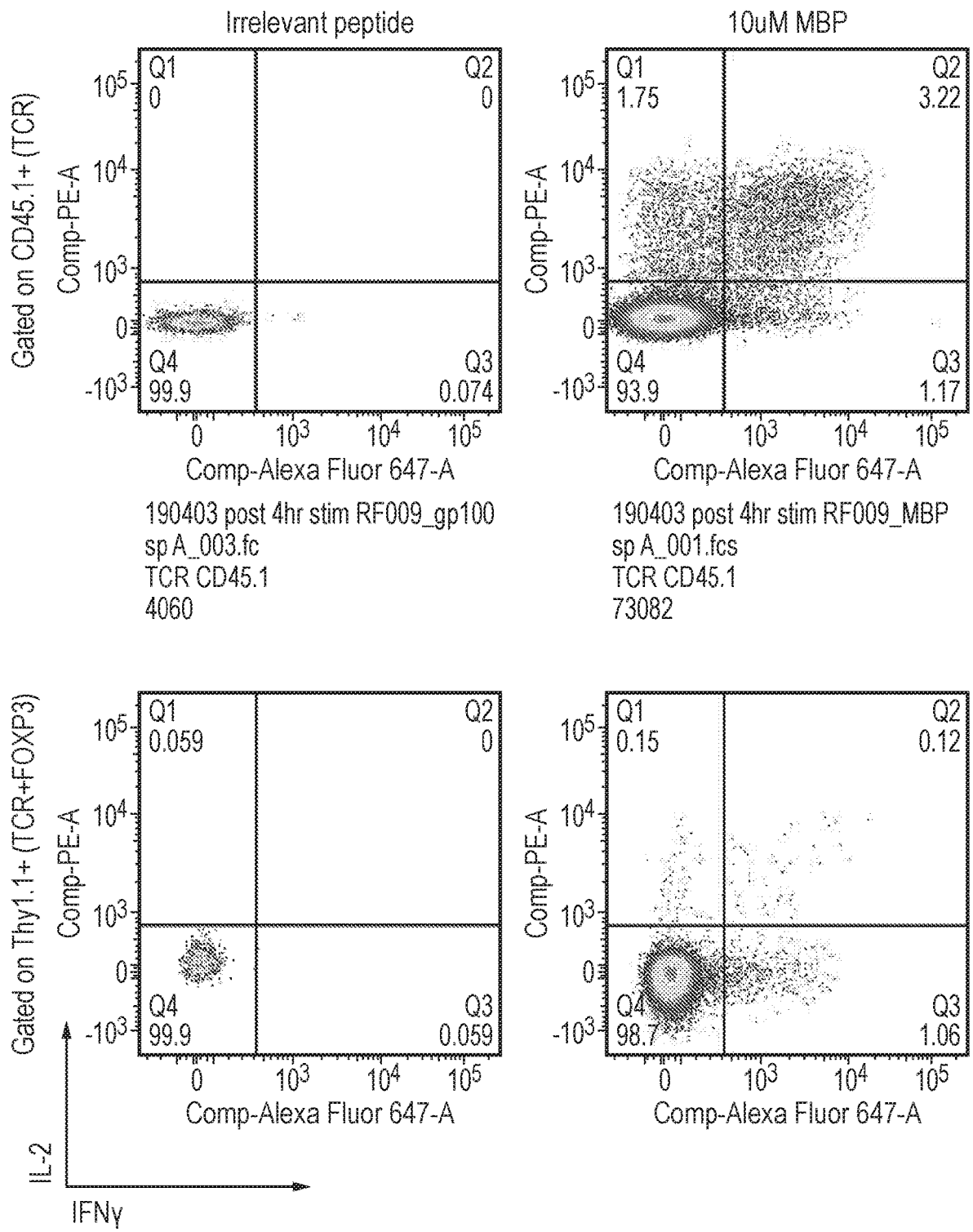
Figure 10B:
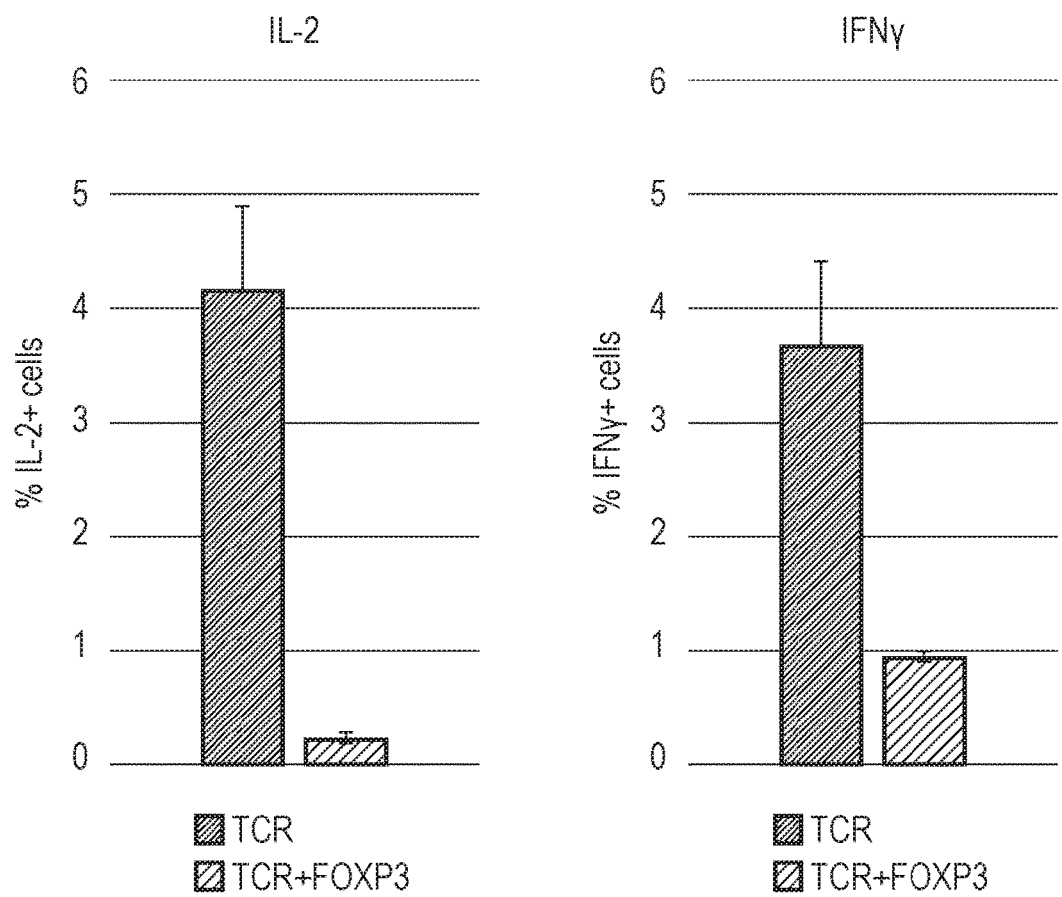

FIG. 10—Treg expressing exogenous FOXP3 retain Treg functionality after 7 weeks in vivo whilst Tregs not expressing exogenous FOXP3 acquire the ability to produce effector cytokines A Splenocytes were cultured for 4 hours with CD86+ HLA-DR4+CHO cells pulsed with irrelevant peptide or 10 uM MBP. Production of IL-2 and IFNg was determined by flow cytometry. FACS plots show CD45.1 cells (top panel) containing Treg expressing TCR alone and Thy1.1 cells containing Treg expressing TCR+FOXP3. B Graphs show cumulative IL-2 and IFNg production by TCR-expressing (dark grey) and TCR+FOXP3-expressing (light grey) Treg. Error bars show standard deviation of the mean (n=3)

Figure 11:
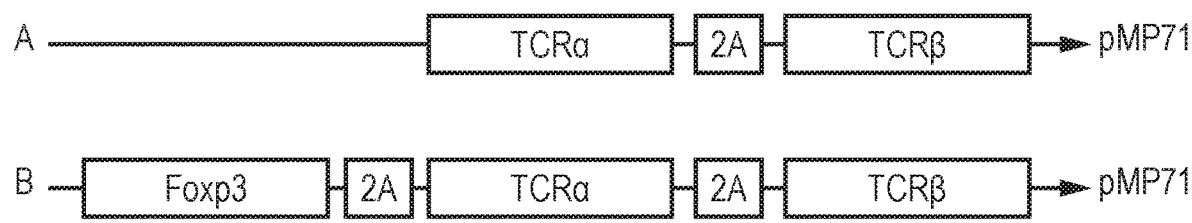

FIG. 11—shows a schematic diagram of an illustrative retroviral vector encoding (A) TCR alpha and beta chains and (B) FOXP3 plus TCR alpha and beta chains.

DETAILED DESCRIPTION

The invention provides a method for enhancing the ability of a regulatory T cell (Tregs) to suppress immune responses comprising increasing FOXP3 expression the Treg.

Regulatory T Cells

The term "regulatory T cell" (Treg) means a T cell which expresses the markers CD4, CD25 and FOXP3 (CD4$^+$ CD25$^+$FOXP3$^+$). Tregs may be identified using the cell surface markers CD4 and CD25 in the absence of or in combination with low-level expression of the surface protein CD127 (CD4$^+$CD25$^+$CD127$^-$ or CD4$^+$CD25$^+$CD127$^{low}$). Tregs may also express on the cell surface high levels of CTLA-4 (cytotoxic T-lymphocyte associated molecule-4) or GITR (glucocorticoid-induced TNF receptor). Unlike conventional T cells, Tregs do not produce IL-2 and are therefore anergic at baseline.

The term "natural Treg" means a thymus-derived Treg. Natural Tregs are CD4$^+$CD25$^+$FOXP3$^+$Helios$^+$Neuropilin1$^+$. The term "natural Treg" distinguishes thymus-derived Tregs from "induced Tregs", which develop from conventional T cells outside the thymus. Compared with induced Tregs, natural Tregs have higher expression of PD-1 (programmed cell death-1, pdcd1), neuropilin 1 (Nrp1), Helios (Ikzf2), and CD73. Natural Tregs may be distinguished from induced Tregs on the basis of the expression of Helios protein or Neuropilin 1 (Nrp1) individually.

As used herein, the term "induced regulatory T cell" (iTreg) means a CD4$^+$ CD25$^+$ FOXP3$^+$ Helios$^-$ Neuropilin 1$^-$ T cell which develops from mature CD4+ conventional T cells outside of the thymus. For example, iTregs can be induced in vitro from CD4+ CD25–FOXP3– cells in the presence of IL-2 and TGF-β.

Suitably, the Treg expresses FOXP3 from the endogenous FoxP3 gene of the cell.

Suitably, the Treg may be a CD4$^+$CD25$^+$FOXP3$^+$ Treg.

Suitably, the Treg may be a CD4$^+$CD25$^+$CD127$^-$ Treg.

Suitably, the Treg may be a CD4$^+$CD25$^+$CD127$^{low}$ Treg.

Suitably, the Treg may be a CD4$^+$CD25$^+$CD127$^-$ CD45RA$^+$ Treg.

Suitably, the Treg may be a CD4$^+$CD25$^+$ CD127$^{low}$CD45RA$^+$ Treg

Suitably, the Treg may be a CD4$^+$CD25$^+$FOXP3$^+$CD127$^-$ Treg.

Suitably, the Treg may be a CD4$^+$CD25$^+$FOXP3$^+$ CD127$^{low}$ Treg.

Suitably, the Treg is a CD4$^+$CD25$^+$FOXP3$^+$Helios$^+$ Treg.

Suitably, the Treg is a CD4$^+$CD25$^+$FOXP3$^+$Neuropilin 1$^+$ Treg.

Suitably, the Treg is a CD4$^+$CD25$^+$FOXP3$^+$Helios$^+$Neuropilin 1$^+$ Treg.

Suitably, the Treg is a human Treg. Suitably the Treg is a human Treg and the FOXP3 is human FOXP3.

The term "Tconv cells", meaning conventional T cells, refers to T cells that are not Tregs.

In one aspect, the Treg of the present invention may be derived from a stem cell. In particular, the Treg of the present invention may be derived from a stem cell in vitro.

In another aspect, the cell is a progenitor cell.

As used herein, the term "stem cell" means an undifferentiated cell which is capable of indefinitely giving rise to more stem cells of the same type, and from which other, specialised cells may arise by differentiation. Stem cells are multipotent. Stem cells may be for example, embryonic stem cells or adult stem cells.

As used herein, the term "progenitor cell" means a cell which is able to differentiate to form one or more types of cells but has limited self-renewal in vitro.

Suitably, the cell is capable of being differentiated into a T cell, such as a Treg.

Suitably, the cell has the ability to differentiate into a T cell, which expresses FOXP3 such as a Treg.

Suitably, the cell may be an embryonic stem cell (ESC). Suitably, the cell is a haematopoietic stem cell or haematopoietic progenitor cell. Suitably, the cell is an induced pluripotent stem cell (iPSC). Suitably, the cell may be obtained from umbilical cord blood. Suitably, the cell may be obtained from adult peripheral blood.

In some aspects, hematopoietic stem and progenitor cell (HSPCs) may be obtained from umbilical cord blood. Cord blood can be harvested according to techniques known in the art (e.g., U.S. Pat. Nos. 7,147,626 and 7,131,958 which are incorporated herein by reference).

In one aspect, HSPCs may be obtained from pluripotent stem cell sources, e.g., induced pluripotent stem cells (iPSCs) and embryonic stem cells (ESCs).

As used herein, the term "hematopoietic stem and progenitor cell" or "HSPC" refers to a cell which expresses the antigenic marker CD34 (CD34+) and populations of such cells. In particular embodiments, the term "HSPC" refers to a cell identified by the presence of the antigenic marker CD34 (CD34+) and the absence of lineage (lin) markers. The population of cells comprising CD34+ and/or Lin(–) cells includes haematopoietic stem cells and hematopoietic progenitor cells.

HSPCs can be obtained or isolated from bone marrow of adults, which includes femurs, hip, ribs, sternum, and other bones. Bone marrow aspirates containing HSPCs can be obtained or isolated directly from the hip using a needle and syringe. Other sources of HSPCs include umbilical cord blood, placental blood, mobilized peripheral blood, Wharton's jelly, placenta, fetal blood, fetal liver, or fetal spleen. In particular embodiments, harvesting a sufficient quantity of HSPCs for use in therapeutic applications may require mobilizing the stem and progenitor cells in the subject.

As used herein, the term "induced pluripotent stem cell" or "iPSC" refers to a non-pluripotent cell that has been reprogrammed to a pluripotent state. Once the cells of a subject have been reprogrammed to a pluripotent state, the cells can then be programmed to a desired cell type, such as a hematopoietic stem or progenitor cell (HSC and HPC respectively).

As used herein, the term "reprogramming" refers to a method of increasing the potency of a cell to a less differentiated state.

As used herein, the term "programming" refers to a method of decreasing the potency of a cell or differentiating the cell to a more differentiated state.

Immune Responses

The expression "enhancing the ability to suppress immune responses" means to increase the suppressive effect of a Treg (or population of such Tregs) on an immune response in comparison to the suppressive effect of a corresponding Treg which has not been modified by a method of the invention (or population of such Tregs).

The term "immune response" refers to a number of physiological and cellular effects facilitated by the immune system in response to a stimulus such as a pathogen or an autoantigen. Examples of such effects include increased proliferation of Tconv cells and secretion of cytokines. Any such effects may be used as indicators of the strength of an immune response. A relatively weaker immune response by Tconv in the presence of modified Tregs compared to non-modified Treg would indicate a relative enhancement of the modified Tregs to suppress immune responses. For example, a relative decrease in cytokine secretion would be indicative of a weaker immune response, and thus an enhancement of the ability of Tregs to suppress immune responses.

Assays are known in the art for measuring indicators of immune response strength, and thereby the suppressive ability of Tregs. In particular, antigen-specific Tconv cells may be co-cultured with Tregs, and a peptide of the corresponding antigen added to the co-culture to stimulate a response from the Tconv cells. The degree of proliferation of the Tconv cells and/or the quantity of the cytokine IL-2 they secrete in response to addition of the peptide may be used as indicators of the suppressive abilities of the co-cultured Tregs.

Antigen-specific Tconv cells co-cultured with Tregs of the present invention having increased FOXP3 expression may proliferate 5, 10, 15, 20, 25, 30, 35 or 40% less than the same Tconv cells co-cultured with corresponding Tregs that do not have increased FOXP3 expression.

Antigen-specific Tconv cells co-cultured with Tregs of the invention having increased FOXP3 expression may show a reduction of effector cytokine that is at least 10%, at least 20%, at least 30%, at least 40%, at least 50%, or at least 60% greater than corresponding Tconv cells co-cultured with corresponding Tregs that do not have increased FOXP3 expression.

Antigen-specific Tconv cells co-cultured with Tregs of the invention having increased FOXP3 expression may produce 10%, 20%, 30%, 40%, 50%, 60% or less effector cytokine than than corresponding Tconv cells co-cultured with corresponding Tregs that do not have increased FOXP3 expression.

The effector cytokine may be selected from IL-2, IL-17, TNFα, GM-CSF, IFN-γ, IL-4, IL-5, IL-9, IL-10 and IL-13.

Suitably the effector cytokine may be selected from IL-2, IL-17, TNFα, GM-CSF and IFN-γ.

Antigen-specific Tconv cells co-cultured with Tregs of the invention having increased FOXP3 expression may achieve suppression of IL-2 production at ½, ¼, ⅛, 1/10 or 1/20 the cell number of corresponding Tregs that do not have increased FOXP3 expression.

FOXP3

"FOXP3" is the abbreviated name of the forkhead box P3 protein. FOXP3 is a member of the FOX protein family of transcription factors and functions as a master regulator of the regulatory pathway in the development and function of regulatory T cells.

"Increasing FOXP3 expression" means to increase the levels of FOXP3 mRNA and/or protein in a Treg (or population of such Tregs) in comparison to a corresponding Treg which has not been modified by a method of the invention (or population of such Tregs). For example, the level of FOXP3 mRNA and/or protein in a Treg modified by a method of the invention (or a population of such Tregs) may be increased to at least 1.5-fold, at least 2-fold, at least 5-fold, at least 10-fold, at least 50-fold, at least 100-fold, at least 150-fold greater than the level in a corresponding Treg which has not been modified by a method of the invention (or population of such Tregs).

Suitably, the level of FOXP3 mRNA and/or protein in a Treg modified by a method of the invention (or a population of such Tregs) may be increased to at least 1.5-fold greater than the level in a corresponding Treg which has not been modified by a method of the invention (or population of such Tregs).

Suitably, the level of FOXP3 mRNA and/or protein in a Treg modified by a method of the invention (or a population of such Tregs) may be increased to at least 2-fold greater than the level in a corresponding Treg which has not been modified by a method of the invention (or population of such Tregs).

Suitably, the level of FOXP3 mRNA and/or protein in a Treg modified by a method of the invention (or a population of such Tregs) may be increased to at least 5-fold greater than the level in a corresponding Treg which has not been modified by a method of the invention (or population of such Tregs).

Techniques for measuring the levels of specific mRNA and protein are well known in the art. mRNA levels in a population of cells, such as Tregs, may be measured by techniques such as the Affymetrix ebioscience prime flow RNA assay, Northern blotting, serial analysis of gene expression (SAGE) or quantitative polymerase chain reaction (qPCR). Protein levels in a population of cells may be measured by techniques such as flow cytometry, high-performance liquid chromatography (HPLC), liquid chromatography-mass spectrometry (LC/MS), Western blotting or enzyme-linked immunosorbent assay (ELISA).

In some embodiments of the invention, FOXP3 expression is increased by introducing into the isolated Tregs a polynucleotide encoding a FOXP3 polypeptide.

The term "introduce" refers to methods for inserting foreign DNA into a cell, including both transfection and transduction methods. Transfection is the process of introducing nucleic acids into a cell by non-viral methods. Transduction is the process of introducing foreign DNA into a cell via a viral vector.

A "FOXP3 polypeptide" is a polypeptide having FOXP3 activity i.e. a polypeptide able to bind FOXP3 target DNA and function as a transcription factor regulating development and function of Tregs. Techniques for measuring transcription factor activity are well known in the art. For example, transcription factor DNA-binding activity may be measured by ChIP. The transcription regulatory activity of a transcription factor may be measured by quantifying the level of expression of genes which it regulates. Gene expression may be quantified by measuring the levels of mRNA and/or protein produced from the gene using techniques such as Northern blotting, SAGE, qPCR, HPLC, LC/MS, Western blotting or ELISA. Genes regulated by FOXP3 include cytokines such as IL-2, IL-4 and IFN-γ (Siegler et al. Annu. Rev. Immunol. 2006, 24: 209-26, incorporated herein by reference).

Polynucleotides and Polypeptides

The terms "polynucleotide" and "nucleic acid" are intended to be synonymous with each other. A polynucleotide may be any suitable type of nucleotide sequence, such as a synthetic RNA/DNA sequence, a cDNA sequence or a partial genomic DNA sequence.

The term "polypeptide" is synonymous with "protein" and means a series of residues, typically L-amino acids, connected to one another typically by peptide bonds between the α-amino and carboxyl groups of adjacent amino acids.

Numerous different polynucleotides can encode the same polypeptide as a result of the degeneracy of the genetic code. The skilled person may make nucleotide substitutions that do not affect the polypeptide sequence encoded by the polynucleotides to reflect the codon usage of any particular host organism in which the polypeptides are to be expressed.

The polynucleotide may comprise DNA or RNA, may be single-stranded or double-stranded and may include synthetic or modified nucleotides. A number of different types of modification to oligonucleotides are known in the art. These include methylphosphonate and phosphorothioate backbones, addition of acridine or polylysine chains at the 3' and/or 5' ends of the molecule. Polynucleotides may be modified by any method in the art. Such modifications may enhance the in vivo activity or life span of the polynucleotide.

The polynucleotide may be in isolated or recombinant form. It may be incorporated into a vector and the vector may be incorporated into a host cell.

The polynucleotide may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. Suitably, the polynucleotide may be codon optimised for expression in a murine model of disease. Suitably, the polynucleotide may be codon optimised for expression in a human subject.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms. Codon optimisation may also involve the removal of mRNA instability motifs and cryptic splice sites.

FOXP3 Polypeptide Sequences

Suitably, the FOXP3 polypeptide may comprise the polypeptide sequence of a human FOXP3, such as UniProtKB accession Q9BZS1, or a functional fragment thereof:

(SEQ ID NO: 3)
MPNPRPGKPSAPSLALGPSPGASPSWRAAPKASDLLGARGPGGTFQGRDL

RGGAHASSSSLNPMPPSQLQLPTLPLVMVAPSGARLGPLPHLQALLQDRP

HFMHQLSTVDAHARTPVLQVHPLESPAMISLTPPTTATGVFSLKARPGLP

PGINVASLEWVSREPALLCTFPNPSAPRKDSTLSAVPQSSYPLLANGVCK

WPGCEKVFEEPEDFLKHCQADHLLDEKGRAQCLLQREMVQSLEQQLVLEK

EKLSAMQAHLAGKMALTKASSVASSDKGSCCIVAAGSQGPVVPAWSGPRE

APDSLFAVRRHLWGSHGNSTFPEFLHNMDYFKFHNMRPPFTYATLIRWAI

LEAPEKQRTLNEIYHWFTRMFAFFRNHPATWKNAIRHNLSLHKCFVRVES

EKGAVWTVDELEFRKKRSQRPSRCSNPTPGP

In some embodiments of the invention, the FOXP3 polypeptide comprises an amino acid sequence which is at least 80% identical to SEQ ID NO: 3 or a functional fragment thereof. Suitably, the FOXP3 polypeptide comprises an amino acid sequence which is at least 85, 90, 95, 98 or 99% identical to SEQ ID NO: 3 or a functional fragment thereof. In some embodiments, the FOXP3 polypeptide comprises SEQ ID NO: 3 or a functional fragment thereof.

Suitably, the FOXP3 polypeptide may be a variant of SEQ ID NO: 3, for example a natural variant. Suitably, the FOXP3 polypeptide is an isoform of SEQ ID NO: 3. For example, the FOXP3 polypeptide may comprise a deletion of amino acid positions 72-106 relative to SEQ ID NO: 3. Alternatively, the FOXP3 polypeptide may comprise a deletion of amino acid positions 246-272 relative to SEQ ID NO: 3.

Suitably, the FOXP3 polypeptide comprises SEQ ID NO: 4 or a functional fragment thereof:

(SEQ ID NO: 4)
MPNPRPGKPSAPSLALGPSPGASPSWRAAPKASDLLGARGPGGTFQGRDL

RGGAHASSSSLNPMPPSQLQLPTLPLVMVAPSGARLGPLPHLQALLQDRP

HFMHQLSTVDAHARTPVLQVHPLESPAMISLTPPTTATGVFSLKARPGLP

PGINVASLEWVSREPALLCTFPNPSAPRKDSTLSAVPQSSYPLLANGVCK

WPGCEKVFEEPEDFLKHCQADHLLDEKGRAQCLLQREMVQSLEQVEELSA

MQAHLAGKMALTKASSVASSDKGSCCIVAAGSQGPVVPAWSGPREAPDSL

FAVRRHLWGSHGNSTFPEFLHNMDYFKFHNMRPPFTYATLIRWAILEAPE

KQRTLNEIYHWFTRMFAFFRNHPATWKNAIRHNLSLHKCFVRVESEKGAV

WTVDELEFRKKRSQRPSRCSNPTPGPEGRGSLLTCGDVEEN.

Suitably the FOXP3 polypeptide comprises an amino acid sequence which is at least 80% identical to SEQ ID NO: 4 or a functional fragment thereof. Suitably, the polypeptide comprises an amino acid sequence which is 85, 90, 95, 98 or 99% identical to SEQ ID NO: 4 or a functional fragment thereof.

Suitably, the FOXP3 polypeptide may be a variant of SEQ ID NO: 4, for example a natural variant. Suitably, the FOXP3 polypeptide is an isoform of SEQ ID NO: 4 or a functional fragment thereof. For example, the FOXP3 polypeptide may comprise a deletion of amino acid positions 72-106 relative to SEQ ID NO: 4. Alternatively, the FOXP3 polypeptide may comprise a deletion of amino acid positions 246-272 relative to SEQ ID NO: 4.

FOXP3 Polynucleotide Sequences

Suitably, the FOXP3 polypeptide is encoded by the polynucleotide sequence set forth in SEQ ID NO: 1:

(SEQ ID NO: 1)
ATGCCCAACCCCAGGCCTGGCAAGCCCTCGGCCCCTTCCTTGGCCCTTGG

CCCATCCCCAGGAGCCTCGCCCAGCTGGAGGGCTGCACCCAAAGCCTCAG

ACCTGCTGGGGGCCCGGGGCCCAGGGGGAACCTTCCAGGGCCGAGATCTT

CGAGGCGGGGCCCATGCCTCCTCTTCTTCCTTGAACCCCATGCCACCATC

GCAGCTGCAGCTGCCCACACTGCCCCTAGTCATGGTGGCACCCTCCGGGG

CACGGCTGGGCCCCTTGCCCCACTTACAGGCACTCCTCCAGGACAGGCCA

CATTTCATGCACCAGCTCTCAACGGTGGATGCCCACGCCCGGACCCCTGT

GCTGCAGGTGCACCCCCTGGAGAGCCCAGCCATGATCAGCCTCACACCAC

CCACCACCGCCACTGGGGTCTTCTCCCTCAAGGCCCGGCCTGGCCTCCCA

CCTGGGATCAACGTGGCCAGCCTGGAATGGGTGTCCAGGGAGCCGGCACT

GCTCTGCACCTTCCCAAATCCCAGTGCACCCAGGAAGGACAGCACCCTTT

CGGCTGTGCCCCAGAGCTCCTACCCACTGCTGGCAAATGGTGTCTGCAAG

TGGCCCGGATGTGAGAAGGTCTTCGAAGAGCCAGAGGACTTCCTCAAGCA

CTGCCAGGCGGACCATCTTCTGGATGAGAAGGGCAGGGCACAATGTCTCC

TCCAGAGAGAGATGGTACAGTCTCTGGAGCAGCAGCTGGTGCTGGAGAAG

-continued

```
GAGAAGCTGAGTGCCATGCAGGCCCACCTGGCTGGGAAAATGGCACTGAC

CAAGGCTTCATCTGTGGCATCATCCGACAAGGGCTCCTGCTGCATCGTAG

CTGCTGGCAGCCAAGGCCCTGTCGTCCCAGCCTGGTCTGGCCCCCGGGAG

GCCCCTGACAGCCTGTTTGCTGTCCGGAGGCACCTGTGGGGTAGCCATGG

AAACAGCACATTCCCAGAGTTCCTCCACAACATGGACTACTTCAAGTTCC

ACAACATGCGACCCCCTTTCACCTACGCCACGCTCATCCGCTGGGCCATC

CTGGAGGCTCCAGAGAAGCAGCGGACACTCAATGAGATCTACCACTGGTT

CACACGCATGTTTGCCTTCTTCAGAAACCATCCTGCCACCTGGAAGAACG

CCATCCGCCACAACCTGAGTCTGCACAAGTGCTTTGTGCGGGTGGAGAGC

GAGAAGGGGGCTGTGTGGACCGTGGATGAGCTGGAGTTCCGCAAGAAACG

GAGCCAGAGGCCCAGCAGGTGTTCCAACCCTACACCTGGCCCCTGA
```

In some embodiments of the invention, the polynucleotide encoding the FOXP3 polypeptide or variant comprises a polynucleotide sequence which is at least 80% identical to SEQ ID NO: 1 or a functional fragment thereof. Suitably, the polynucleotide encoding the FOXP3 polypeptide or variant comprises a polynucleotide sequence which is at least 85, 90, 95, 98 or 99% identical to SEQ ID NO: 1 or a functional fragment thereof. In some embodiments of the invention, the polynucleotide encoding the FOXP3 polypeptide or variant comprises SEQ ID NO: 1 or a functional fragment thereof.

Suitably, the FOXP3 polypeptide is encoded by the polynucleotide sequence set forth in SEQ ID NO: 2:

```
                                             (SEQ ID NO: 2)
GAATTCGTCGACATGCCCAACCCCAGACCCGGCAAGCCTTCTGCCCCTTC

TCTGGCCCTGGGACCATCTCCTGGCGCCTCCCCATCTTGGAGAGCCGCCC

CTAAAGCCAGCGATCTGCTGGGAGCTAGAGGCCCTGGCGGCACATTCCAG

GGCAGAGATCTGAGAGGCGGAGCCCACGCCTCTAGCAGCAGCCTGAATCC

CATGCCCCTAGCCAGCTGCAGCTGCCTACACTGCCTCTCGTGATGGTGG

CCCCTAGCGGAGCTAGACTGGGCCCTCTGCCTCATCTGCAGGCTCTGCTG

CAGGACCGGCCCCACTTTATGCACCAGCTGAGCACCGTGGACGCCCACGC

CAGAACACCTGTGCTGCAGGTGCACCCCCTGGAAAGCCCTGCCATGATCA

GCCTGACCCCTCCAACCACAGCCACCGGCGTGTTCAGCCTGAAGGCCAGA

CCTGGACTGCCCCCTGGCATCAATGTGGCCAGCCTGGAATGGGTGTCCCG

CGAACCTGCCCTGCTGTGCACCTTCCCCAATCCTAGCGCCCCAGAAAGG

ACAGCACACTGTCTGCCGTGCCCCAGAGCAGCTATCCCCTGCTGGCTAAC

GGCGTGTGCAAGTGGCCTGGCTGCGAGAAGGTGTTCGAGGAACCCGAGGA

CTTCCTGAAGCACTGCCAGGCCGACCATCTGCTGGACGAGAAAGGCAGAG

CCCAGTGCCTGCTGCAGCGCGAGATGGTGCAGTCCCTGGAACAGCAGCTG

GTGCTGGAAAAAGAAAAGCTGAGCGCCATGCAGGCCCACCTGGCCGGAAA

GATGGCCCTGACAAAAGCCAGCAGCGTGGCCAGCTCCGACAAGGGCAGCT

GTTGTATCGTGGCCGCTGGCAGCCAGGGACCTGTGGTGCCTGCTTGGAGC

GGACCTAGAGAGGCCCCCGATAGCCTGTTTGCCGTGCGGAGACACCTGTG

GGGCAGCCACGGCAACTCTACCTTCCCCGAGTTCCTGCACAACATGGACT
```

```
ACTTCAAGTTCCACAACATGAGGCCCCCCTTCACCTACGCCACCCTGATC

AGATGGGCCATTCTGGAAGCCCCCGAGAAGCAGCGGACCCTGAACGAGAT

CTACCACTGGTTTACCCGGATGTTCGCCTTCTTCCGGAACCACCCCGCCA

CCTGGAAGAACGCCATCCGGCACAATCTGAGCCTGCACAAGTGCTTCGTG

CGGGTGGAAAGCGAGAAGGGCGCCGTGTGGACAGTGGACGAGCTGGAATT

TCGGAAGAAGCGGTCCCAGAGGCCCAGCCGGTGTAGCAATCCTACACCTG

GCCCTGAGGGCAGAGGAAGTCTGCTAACATGCGGTGACGTCGAGGAGAAT

CC.
```

In some embodiments of the invention, the polynucleotide encoding the FOXP3 polypeptide or variant comprises a polynucleotide sequence which is at least 80% identical to SEQ ID NO: 2 or a functional fragment thereof. Suitably, the polynucleotide encoding the FOXP3 polypeptide or variant comprises a polynucleotide sequence which is at least 85, 90, 95, 98 or 99% identical to SEQ ID NO: 2 or a functional fragment thereof. In some embodiments of the invention, the polynucleotide encoding the FOXP3 polypeptide or variant comprises SEQ ID NO: 2 or a functional fragment thereof.

Suitably, the polynucleotide encoding the FOXP3 polypeptide or variant thereof may be codon optimised. Suitably, the polynucleotide encoding the FOXP3 polypeptide or variant thereof may be codon optimised for expression in a human cell.

Sequence Comparisons

Sequence comparisons can be conducted by eye, or more usually, with the aid of readily available sequence comparison programs. These publicly and commercially available computer programs can calculate sequence identity between two or more sequences.

Sequence identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible (reflecting higher relatedness between the two compared sequences) will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified.

However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % sequence identity therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387 incorporated herein by reference). Examples of other software than can perform sequence comparisons include, but are not limited to, the BLAST package (see Ausubel et al., 1999 ibid—Chapter 18), FASTA (Atschul et al., 1990, J. Mol. Biol., 403-410 incorporated herein by reference) and the GENEWORKS suite of comparison tools. Both BLAST and FASTA are available for offline and online searching (see Ausubel et al., 1999 ibid, pages 7-58 to 7-60 incorporated herein by reference). However it is preferred to use the GCG Bestfit program.

Suitably, the sequence identity may be determined across the entirety of the sequence. Suitably, the sequence identity may be determined across the entirety of the candidate sequence being compared to a sequence recited herein.

Although the final sequence identity can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix (the default matrix for the BLAST suite of programs). GCG Wisconsin programs generally use either the public default values or a custom symbol comparison table if supplied (see user manual for further details). Preferably, the public default values for the GCG package, or in the case of other software the default matrix, such as BLOSUM62, are used.

Once the software has produced an optimal alignment, it is possible to calculate % sequence identity. The software typically does this as part of the sequence comparison and generates a numerical result.

Vector

In some embodiments of the invention the polynucleotide encoding FOXP3 is a contiguous portion of an expression vector.

The term "expression vector" means a construct enabling expression of the FOXP3 polypeptide. Suitably, the expression vector is a cloning vector.

Suitable vectors may include, but are not limited to, plasmids, viral vectors, transposons, or nucleic acid complexed with polypeptide or immobilised onto a solid phase particle.

Preferably, the expression vector is capable of sustained high-level expression in host cells.

The expression vector may be a retroviral vector. The expression vector may be based on or derivable from the MP71 vector backbone. The expression vector may lack a full-length or truncated version of the Woodchuck Hepatitis Response Element (WPRE).

In some embodiments of the invention the vector also encodes a T cell receptor (TCR).

A TCR is a cell surface molecule that binds fragments of antigen bound to major histocompatibility complex (MHC) molecules on antigen presenting cells as part of directing an immune response. Suitably, the TCR may be a recombinant protein, in other words the TCR may be an exogenous protein which is not naturally expressed by the present Treg of the invention.

In some embodiments of the invention the vector also encodes a chimeric antigen receptor (CAR).

A CAR is a recombinant cell surface molecule expressed by an engineered T cell that binds antigen expressed on the surface of other cells as part of directing an immune response. More particularly, CARs are proteins which graft the specificity of an antigen binder, such as a monoclonal antibody (mAb), to the effector function of a T-cell. Their usual form is that of a type I transmembrane domain protein with an antigen recognizing amino terminus, a spacer, a transmembrane domain all connected to a compound endodomain which transmits T-cell survival and activation signals.

Where the vector comprises a polynucleotide encoding a TCR or CAR in addition to a polynucleotide encoding FOXP3; the vector may have the orientation of: 5' FOXP3-TCR/CAR 3'. Accordingly the polynucleotide encoding a FOXP3 may be 5' to the polynucleotide encoding CAR or TCR.

Suitably, the polynucleotide encoding FOXP3 may be separated from the polynucleotide encoding a TCR or CAR by a nucleic acid sequence which enables both the nucleic acid sequence encoding FOXP3 and the nucleic acid sequence encoding the TCR or CAR to be expressed from the same mRNA transcript.

For example, the polynucleotide may comprise an internal ribosome entry site (IRES) between the nucleic acid sequences which encode (i) FOXP3 and (ii) the TCR or CAR. An IRES is a nucleotide sequence that allows for translation initiation in the middle of a mRNA sequence.

The polynucleotide may comprise a nucleic acid sequence encoding (i) FOXP3 and (ii) the TCR or CAR linked by an internal self-cleaving sequence.

Suitably, the vector may have the structure: 5' Strong promoter (e.g. LTR)-FoxP3-2A-CAR/TCR-3'LTR. Here, FOXP3 expression is directly driven by the strong LTR promoter for optimal expression. CAR/TCR is preceded by a 2A sequence and expression of the CAR/TCR is thus dependent on both LTR promoter activity and 2A cleavage activity.

Importantly, a configuration in which FOXP3 precedes CAR/TCR in the 5' to 3' direction ensures that CAR/TCR expression can only occur when FOXP3 has been expressed and that expression of CAR/TCR without FOXP3 does not occur. This is a particular advantage in the present context of an engineered Treg, as it reduces the risk of an engineered Treg acquiring an effector phenotype and/or reduces the risk associated with introducing the CAR or TCR into a T effector cell present in a starting population.

The internal self-cleaving sequence may be any sequence which enables the polypeptide comprising (i) FOXP3 and (ii) the TCR or CAR to become separated.

The cleavage site may be self-cleaving, such that when the polypeptide is produced, it is immediately cleaved into individual peptides without the need for any external cleavage activity.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide, various models have been proposed for to account for the "cleavage" activity: proteolysis by a host-cell proteinase, autoproteolysis or a translational effect (Donnelly et al (2001) J. Gen.

Virol. 82:1027-1041 incorporated herein by reference). The exact mechanism of such "cleavage" is not important for the purposes of the present invention, as long as the cleavage site, when positioned between nucleic acid sequences which encode proteins, causes the proteins to be expressed as separate entities.

The self-cleaving peptide may be a 2A self-cleaving peptide from an aphtho- or a cardiovirus.

A variant can be considered in terms of similarity (i.e. amino acid residues having similar chemical properties/functions), preferably a variant is expressed in terms of sequence identity.

Sequence comparisons can be conducted by eye, or more usually, with the aid of readily available sequence comparison programs. These publicly and commercially available computer programs can calculate sequence identity between two or more sequences.

Suitably, the FOXP3 polypeptide expressed from the present vector may be positioned at the N-terminal of a self-cleaving peptide, for example a 2A self-cleaving peptide. Such a FOXP3-2A polypeptide may comprise a sequence shown as SEQ ID NO: 5 or 6; or a variant of SEQ ID NO: 5 or 6 which is at least 80% identical thereto. Suitably, the variant may be at least 85, 90, 95, 98 or 99% identical to SEQ ID NO: 5 or 6.

SEQ ID NO: 5
MPNPRPGKPSAPSLALGPSPGASPSWRAAPKASDLLGARGPGGTFQGRDL

RGGAHASSSSLNPMPPSQLQLPTLPLVMVAPSGARLGPLPHLQALLQDRP

HFMHQLSTVDAHARTPVLQVHPLESPAMISLTPPTTATGVFSLKARPGLP

PGINVASLEWVSREPALLCTFPNPSAPRKDSTLSAVPQSSYPLLANGVCK

WPGCEKVFEEPEDFLKHCQADHLLDEKGRAQCLLQREMVQSLEQQLVLEK

EKLSAMQAHLAGKMALTKASSVASSDKGSCCIVAAGSQGPVVPAWSGPRE

APDSLFAVRRHLWGSHGNSTFPEFLHNMDYFKFHNMRPPFTYATLIRWAI

LEAPEKQRTLNEIYHWFTRMFAFFRNHPATWKNAIRHNLSLHKCFVRVES

EKGAVWTVDELEFRKKRSQRPSRCSNPTPGPGATNFSLLKQAGDVEENPG

PS

SEQ ID NO: 6
MPNPRPGKPSAPSLALGPSPGASPSWRAAPKASDLLGARGPGGTFQGRDL

RGGAHASSSSLNPMPPSQLQLPTLPLVMVAPSGARLGPLPHLQALLQDRP

HFMHQLSTVDAHARTPVLQVHPLESPAMISLTPPTTATGVFSLKARPGLP

PGINVASLEWVSREPALLCTFPNPSAPRKDSTLSAVPQSSYPLLANGVCK

WPGCEKVFEEPEDFLKHCQADHLLDEKGRAQCLLQREMVQSLEQVEELSA

MQAHLAGKMALTKASSVASSDKGSCCIVAAGSQGPVVPAWSGPREAPDSL

FAVRRHLWGSHGNSTFPEFLHNMDYFKFHNMRPPFTYATLIRWAILEAPE

KQRTLNEIYHWFTRMFAFFRNHPATWKNAIRHNLSLHKCFVRVESEKGAV

WTVDELEFRKKRSQRPSRCSNPTPGPEGRGSLLTCGDVEENGATNFSLLK

QAGDVEENPGPS

Viral Transduction

In some embodiments of the invention, the polynucleotide encoding FOXP3 is introduced into the isolated Tregs by viral transduction.

Viral delivery systems include but are not limited to adenovirus vector, an adeno-associated viral (AAV) vector, a herpes viral vector, retroviral vector, lentiviral vector, baculoviral vector.

In some embodiments, the polynucleotide encoding FOXP3 is introduced into the isolated Tregs by retroviral transduction.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al. ("Retroviruses" 1997 Cold Spring Harbour Laboratory Press Eds: J M Coffin, SM Hughes, HE Varmus pp 758-763, incorporated herein by reference).

Lentiviruses also belong to the retrovirus family, but they can infect both dividing and non-dividing cells (Lewis et al. 1992 EMBO J. 3053-3058, incorporated herein by reference).

For efficient infection of human cells, viral particles may be packaged with amphotropic envelopes or gibbon ape leukemia virus envelopes.

Isolating Tregs

In some embodiments, the method according to the invention comprises:

(a) isolating the Treg from a cell population; and
(b) increasing FOXP3 expression in the Treg.

The expression "isolating the Treg from a cell population" means to separate out the Treg from a heterogeneous mixture of multiple different types of cells. Suitable the cell population is from a sample from a human subject.

Suitably, the Treg is isolated as a population of Tregs.

Suitably, the population of Tregs comprises at least 70% Tregs, such as 75%, 85%, 90% or 95% Tregs.

In some embodiments of the invention, the cell population comprises or consists of peripheral blood mononuclear cells (PBMCs).

A PBMC is any blood cell with a round nucleus found within the circulating pool of blood, rather than sequestered in the bone marrow, liver, spleen or lymphatic system. PBMCs consist of monocytes and lymphocytes (T cells, B cells and NK cells). Techniques for isolation of PBMCs from whole blood are known in the art. For example, PBMCs can be separated from a blood sample by addition of a density gradient medium, such as Ficoll (GE Healthcare), followed by centrifugation. The different types of cells in the blood separate out into different layers, including a layer containing the PBMCs.

In some embodiments of the invention, isolating the Treg comprises isolating CD4$^+$ T cells. In some embodiments, isolating the Treg comprises isolating CD4$^+$ T cells and subsequently isolating the Treg from the CD4$^+$ T cells.

CD4 (cluster of differentiation 4) is a co-receptor of the T cell receptor expressed by various types of T cells. Isolation of CD4$^+$ cells separates T cells, including Tregs, from the initial cell population. The Tregs may then be isolated from this T cell-enriched population.

Techniques for isolating specific cell types from a heterogeneous population of cells are known in the art. Examples include use of immuno-magnetic beads and fluorescence-activated cell sorting.

In some embodiments of the invention, isolating the population of Tregs comprises using immuno-magnetic beads. Various companies (e.g. Miltenyi Biotec, Stem Cell Technologies, ThermoFisher Scientific) offer kits comprising immuno-magnetic beads for isolation of specific types of T cells (see, for example, Fallarino et al. (2003) Modulation of tryptophan catabolism by regulatory T cells. Nat. Immunol. 4: 1206-1212, incorporated herein by reference). These isolation kits make use of antibodies widely available in the art to T cell surface proteins such as CD8, CD25, CD49b and others. For example, $CD4^+$ cells may be first negatively selected by incubating the cell population with biotin-conjugated antibodies to markers of non-$CD4^+$ cells (e.g. CD8) and removing these cells using anti-biotin magnetic beads. Then, Tregs may be positively selected by incubation with anti-CD25-labelled beads.

In some embodiments of the invention, isolating the population of Tregs comprises fluorescence-activated cell sorting (FACS). In some embodiments, the Tregs are sorted according to their $CD4^+CD25^{hi}CD127^-$ phenotype.

Natural Tregs may be sorted from induced Tregs on the basis of expression of Helios protein or Neuropilin 1. In some embodiments of the invention, the natural Tregs may be sorted according to their $CD4^+CD25^+FOXP3^+Helios^+Neuropilin1^+$ phenotype.

FACS is a form of flow cytometry which is well-known in the art. During FACS, cells are suspended in fluid and streamed through a detection system that analyses various characteristics. Cells can be sorted according to their characteristics using this method. In particular, in FACS, molecules are marked using fluorescent antibodies and cells sorted according to their degree of fluorescence, which indicates level of expression of the particular molecule (see Adan et al. Flow cytometry: basic principles and applications Crit. Rev. Biotechnol. 2017 March; 37(2):163-176, incorporated herein by reference).

Engineered Tregs

The invention also provides an engineered Treg, such as engineered Treg produced by the method of the invention.

The term "engineered Treg" means a Treg that has been manipulated by human intervention such that its gene expression has been altered.

The invention also provides an engineered Treg having higher FOXP3 expression than a non-engineered Treg.

The invention also provides a Treg having higher FOXP3 expression than a corresponding, non-engineered Treg.

"Higher FOXP3 expression" means levels of FOXP3 mRNA or protein in the engineered Treg are higher than they were before the Treg was manipulated by human intervention to alter its gene expression.

The "higher FOXP3 expression" may be defined and determined as described herein.

Suitably, the level of CD25 mRNA and/or protein in a Treg modified by a method of the invention (or a population of such Tregs) may be increased to at least 1.5-fold greater than the level in a corresponding Treg which has not been modified by a method of the invention (or population of such Tregs).

Suitably, the level of CD25 mRNA and/or protein in a Treg modified by a method of the invention (or a population of such Tregs) may be increased to at least 2-fold greater than the level in a corresponding Treg which has not been modified by a method of the invention (or population of such Tregs).

Suitably, the level of CD25 mRNA and/or protein in a Treg modified by a method of the invention (or a population of such Tregs) may be increased to at least 5-fold greater than the level in a corresponding Treg which has not been modified by a method of the invention (or population of such Tregs).

Suitably, the level of CTLA-4 mRNA and/or protein in a Treg modified by a method of the invention (or a population of such Tregs) may be increased to at least 1.5-fold greater than the level in a corresponding Treg which has not been modified by a method of the invention (or population of such Tregs).

Suitably, the level of CTLA-4 mRNA and/or protein in a Treg modified by a method of the invention (or a population of such Tregs) may be increased to at least 2-fold greater than the level in a corresponding Treg which has not been modified by a method of the invention (or population of such Tregs).

Suitably, the level of CTLA-4 mRNA and/or protein in a Treg modified by a method of the invention (or a population of such Tregs) may be increased to at least 5-fold greater than the level in a corresponding Treg which has not been modified by a method of the invention (or population of such Tregs).

In some embodiments of the invention, the engineered Treg comprises an exogenous polynucleotide encoding a FOXP3 polypeptide.

An "exogenous polynucleotide" is a polynucleotide that originates outside the Treg. The exogenous polynucleotide may be introduced into the Treg as part of an expression vector. Accordingly, the exogenous polynucleotide may be contiguous with expression vector elements, such as a promoter.

In some embodiments of the invention, the FOXP3 polypeptide comprises an amino acid sequence which is at least 80% identical to SEQ ID NO: 3 or 4 or a functional fragment thereof. Suitably, the FOXP3 polypeptide comprises an amino acid sequence which is at least 85, 90, 95, 98 or 99% identical to SEQ ID NO: 3 or 4 or a functional fragment thereof. In some embodiments, the FOXP3 polypeptide comprises SEQ ID NO: 3 or 4 or a functional fragment thereof.

In some embodiments of the invention, the exogenous polynucleotide encoding FOXP3 comprises a polynucleotide sequence which is at least 80% identical to SEQ ID NO: 1 or 2. In some embodiments of the invention, the polynucleotide encoding FOXP3 is identical to SEQ ID NO:1 or 2.

In some embodiments of the invention, the exogenous polynucleotide encoding FOXP3 is a contiguous portion of a vector.

In some embodiments of the invention, the vector also encodes a T cell receptor (TCR).

In some embodiments of the invention, the vector comprises a polynucleotide sequence which is at least 80% identical to SEQ ID NO: 5. In some embodiments of the invention, the vector comprises a polynucleotide sequence identical to SEQ ID NO: 5.

Compositions

The invention also provides a pharmaceutical composition comprising an engineered Treg of the invention.

Such pharmaceutical composition may comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s) and other carrier agents.

The pharmaceutical compositions typically should be sterile and stable under the conditions of manufacture and storage. Formulations for parenteral administration include, but are not limited to, suspensions, solutions, emulsions in oily or aqueous vehicles, pastes, and implantable sustained-release or biodegradable formulations. Sterile injectable formulations may be prepared using a non-toxic parenterally acceptable diluent or solvent. A pharmaceutical composition of the present invention may include pharmaceutically acceptable dispersing agents, wetting agents, suspending agents, isotonic agents, coatings, antibacterial and antifungal agents, carriers, excipients, salts, or stabilizers which are non-toxic to the subjects at the dosages and concentrations employed. Preferably, such a composition can further comprise a pharmaceutically acceptable carrier or excipient for use in the treatment of disease that that is compatible with a given method and/or site of administration, for instance for parenteral (e.g. sub-cutaneous, intradermal, or intravenous injection) or intrathecal administration.

The composition may be produced using current good manufacturing practices (cGMP).

Suitably the pharmaceutical composition comprising an engineered Treg may comprise an organic solvent, such as but not limited to, methyl acetate, dimethyl sulfoxide (DMSO), N,N-dimethylformamide (DMF), dimethoxyethane (DME), and dimethylacetamide, including mixtures or combinations thereof.

Suitably the pharmaceutical composition is endotoxin free.

Prevention and/or Treatment of a Disease

The invention also provides an engineered Treg of the invention, or a pharmaceutical composition of the invention, for use in prevention and/or treatment of a disease.

The invention also provides use of an engineered Treg of the invention in the manufacture of a medicament for prevention and/or treatment of a disease.

The invention also provides a method of prevention and/or treatment of a disease comprising administering to a subject an engineered Treg or a composition of the invention.

Preferably, the method of prevention and/or treatment of a disease comprises administration of a pharmaceutical composition of the present invention to a subject.

The term "treat/treatment/treating" refers to administering an engineered Treg or pharmaceutical composition of the invention to a subject having an existing disease or condition in order to lessen, reduce or improve at least one symptom associated with the disease and/or to slow down, reduce or block the progression of the disease.

"Prevention"/"preventing" (or prophylaxis) refers to delaying or preventing the onset of the symptoms of the disease. Prevention may be absolute (such that no disease occurs) or may be effective only in some individuals or for a limited amount of time.

In some embodiment of the invention, the subject of the method of the invention is a mammal, preferably a cat, dog, horse, donkey, sheep, pig, goat, cow, mouse, rat, rabbit or guinea pig. Preferably the subject is a human.

The administration of a pharmaceutical composition of the invention can be accomplished using any of a variety of routes that make the active ingredient bioavailable. For example, an engineered Treg or pharmaceutical composition can be administered intravenously, intrathecally, by oral and parenteral routes, intranasally, intraperitoneally, subcutaneously, transcutaneously or intramuscularly.

Suitably, the engineered Treg or pharmaceutical composition of the invention is administered intravenously. Suitably, the engineered Treg or pharmaceutical composition of the invention is administered intrathecally.

Typically, a physician will determine the dosage that is most suitable for an individual subject, and the dosage will vary with the age, weight and response of the particular subject. The dosage is such that it is sufficient to reduce and/or prevent disease symptoms.

The skilled person appreciates, for example, that route of delivery (e.g. oral vs. intravenous vs. subcutaneous etc.) may impact the required dosage (and vice versa). For example, where particularly high concentrations of an agent within a particular site or location are desired, focused delivery may be preferred. Other factors to be considered when optimizing routes and/or dosing schedule for a given therapeutic regimen may include, for example, the disease being treated (e.g. type or stage etc.), the clinical condition of a subject (e.g. age, overall health etc.), the presence or absence of combination therapy, and other factors known to medical practitioners.

The dosage is such that it is sufficient to stabilise or improve symptoms of the disease.

The present invention also provides a method for treating and/or preventing a disease, which comprises the step of administering a pharmaceutical composition comprising a cell e.g. a T cell according to the invention to a subject.

Suitably, the method of prevention and/or treatment of a disease of may comprise:
  (i) isolation of Tregs from a subject;
  (ii) introducing a polynucleotide sequence encoding a FOXP3 polypeptide into (i.e. engineering) the Tregs; and
  (iii) administering the engineered Tregs to the subject.

Tregs may be isolated from a patent by taking a blood sample and isolating Tregs from it using techniques known in the art, such as those described in this specification under the heading "Isolating Tregs".

A polynucleotide encoding a FOXP3 polypeptide may be introduced into Tregs using techniques known in the art, such as those described in this specification under the heading "Viral transduction".

Suitably the engineered Tregs may be expanded in vitro before administration to the subject. Tregs may be expanded in vitro by culturing them in TexMACX® media.

Disease

The disease to be treated and/or prevented by the methods and uses of the present invention may be any disease which is associated with a pathological immune response.

The disease may be, for example, a cancer, infectious disease or autoimmune disease.

In some embodiments of the invention, the disease is an autoimmune disease.

The disease may have central nervous system (CNS) involvement of systemic autoimmune and inflammatory disease such as Behcet disease, sarcoidosis, systemic lupus erythematosus, juvenile idiopathic arthritis, scleroderma, and Sjögren syndrome.

The disease may be any disease wherein MBP is an antigen e.g. where MBP is a self-antigen.

Suitably the disease may be an autoimmune and inflammatory central nervous system disease (e.g. chronic neurodegenerative conditions).

Suitably the disease may be a chronic neurodegenerative condition such as multiple sclerosis (MS), Alzheimer's disease, Parkinson's disease, neurotropic viral infections, stroke, paraneoplastic disorders and traumatic brain injury.

In some embodiments of the invention, the disease is multiple sclerosis. Suitably, the disease is chronic progressive multiple sclerosis. Suitably, the disease is relapsing/remitting multiple sclerosis.

Suitably, the disease is present in an HLA-DRB1*0401 positive subject. Suitably, the disease is multiple sclerosis and the subject is HLA-DRB1*0401 positive. Suitably, the disease is chronic progressive multiple sclerosis and the subject is HLA-DRB1*0401 positive. Suitably, the disease is relapsing/remitting multiple sclerosis and the subject is HLA-DRB1*0401 positive.

Multiple Sclerosis

Multiple Sclerosis (MS) is the most common neurological disorder among young adults in Europe and in the USA. MS is characterised as a demyelinating disease and is a chronic degenerative disease of the central nervous system in which gradual destruction of myelin occurs in patches throughout the brain and/or spinal cord, interfering with neural connectivity and causing muscular weakness, loss of coordination and speech and visual disturbances.

Several types or patterns of progression of MS have been identified including, clinically isolated syndrome (CIS), relapsing-remitting MS (RRMS), primary progressive MS (PPMS) and secondary progressive MS (SPMS). For some subjects, the increase or progression of disability is very gradual, and for others it can occur more quickly. In general, however, recovery from attacks become less and less complete, and symptoms tend to increase and disability grows.

Although several disease-modifying treatments (DMTs) have been approved to reduce the frequency of clinical relapses, most subjects continue to clinically deteriorate under current therapy schedules. Autologous haematopoietic stem cell transplantation can have lasting beneficial effects for subjects, but the procedure requires aggressive myeloablative conditioning which is associated with substantial toxicity. Neither DMTs nor stem cell transplantation can mediate antigen-specific suppression of the immunopathology of MS. Without wishing to be bound by theory, in the future, administration of one dose of the engineered Treg of the present invention may provide lasting suppression of MS immunopathology in the absence of systemic side effects. This will have a significant impact on the progression of the disease in people with MS.

Suitably, the engineered Treg or pharmaceutical composition of the present invention may reduce or ameliorate one or more of the symptoms of MS, which include reduced or loss of vision, stumbling and uneven gait, slurred speech, urinary frequency and incontinence, mood changes and depression, muscle spasms and paralysis.

The present invention further provides a method for inducing tolerance to a transplant; treating and/or preventing cellular and/or humoral transplant rejection; treating and/or preventing graft-versus-host disease (GvHD), which comprises the step of administering an engineered Treg or a pharmaceutical composition of the invention to a subject.

As used herein, "inducing tolerance to a transplant" refers to inducing tolerance to a transplanted organ in a recipient. In other words, inducing tolerance to a transplant means to reduce the level of a recipient's immune response to a donor transplant organ. Inducing tolerance to a transplanted organ may reduce the amount of immunosuppressive drugs that a transplant recipient requires, or may enable the discontinuation of immunosuppressive drugs.

In one embodiment, the subject is a transplant recipient undergoing immunosuppression therapy.

The transplant may be selected from a liver, kidney, heart, lung, pancreas, intestine, stomach, bone marrow, vascularized composite tissue graft, and skin transplant.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation and any amino acid sequences are written left to right in amino- to carboxy-terminal orientation.

Where a range of values is provided, each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

The singular forms "a", "an", and "the" include plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Embodiments of the invention may be combined.

The publications discussed herein are provided solely for their disclosure prior to the filing date of the present application. Nothing herein is to be construed as an admission that such publications constitute prior art to the claims appended hereto.

The invention will now be further described by way of Examples, which are meant to serve to assist the skilled person in carrying out the invention and are not intended in any way to limit the scope of the invention.

EXAMPLES

Example 1A—Isolation of Natural Tregs

CD4+ T cells were isolated using a CD4+ Positive selection kit. Cells were subsequently stained with flow cytometry antibodies CD4, CD25 and CD127 before FACS sorting using the BD ARIA. CD4+CD25hiCD127− Treg and CD4+CD25−CD127+ Tconv were collected in polypropylene tubes. Purity of cell sorting was determined by addition of FOXP3 PE antibody. Purity of CD4+CD25+CD127−FOXP3+ cells was routinely >70%.

Example 1B—Transduction of Natural Tregs with FOXP3

On day 0 FACS sorted Treg and Tconv were activated separately for 48 hours by culturing 1:1 with anti-CD3 and anti-CD28 beads. On day 2 cells were counted and resuspended in complete RPMI (Tconv) or Texmacs media (Treg) at $1\times10^6$/mL. Non-tissue culture-treated 24-well plates were pre-prepared by coating with retronectin then subsequently blocked with 2% bovine serum albumin in PBS and washed ×2 with PBS. Final concentration of IL-2 was 300 µ/ml for Tconv and 1000 µ/ml for Treg. Cells were incubated overnight at 37° C. before removing supernatant and supplementing with fresh complete media and IL-2. Media was changed on alternate days.

Tconv cells were grown in RPMI-1640 (Gibco) supplemented with 10% heat inactivated foetal bovine serum; 100 Units/mL penicillin; 100 µg/mL streptomycin; 2 mM L-glutamine. Regulatory T cells were cultured in Texmacs media (Miltenyi) supplemented with 100 Units/mL penicillin; 100 µg/mL streptomycin.

Flow cytometric analysis was performed at day 7-10 to assess level of transduction through expression of murine TCR constant regions and FOXP3.

Example 1C—Proliferation and IL-2 Production of Stimulated Tconv Cells in the Presence of FOXP3-Transduced Natural Tregs On day 10 Chinese Hamster Ovary (CHO) cells transduced with human HLA-DR4 and CD80 or CD86 were loaded with (10 µM/ml) of MBP111-129 (LSRFSWGAE-GQRPGFGYGG). Suspensions were incubated for 2 hours at standard tissue culture conditions before being irradiated, washed and re-suspended at appropriate concentration.

Transduced responder T cells were stained with CFSE cell trace dye in warmed PBS at 37° C. for 3 minutes before addition of equal volumes of warm FBS and a further 3 minute incubation. Cells were washed in 5× volume of complete RPMI media before counting and resuspension at $1\times10^6$ transduced cells/ml. Regulatory T cells were removed from culture, washed and re-suspended at $1\times10^6$ transduced cells/ml in complete RPMI. Cells were plated 1 Treg:0.1 CHO cells:varying ratios of Tconv for 4 days.

On day 4 cells were stained with a viability dye and analysed by flow cytometry. Percentage proliferation was determined by gating on 'live' cells and then the population of cells which had lower CFSE fluorescence relative to cells that were cultured without peptide.

Figure 1:
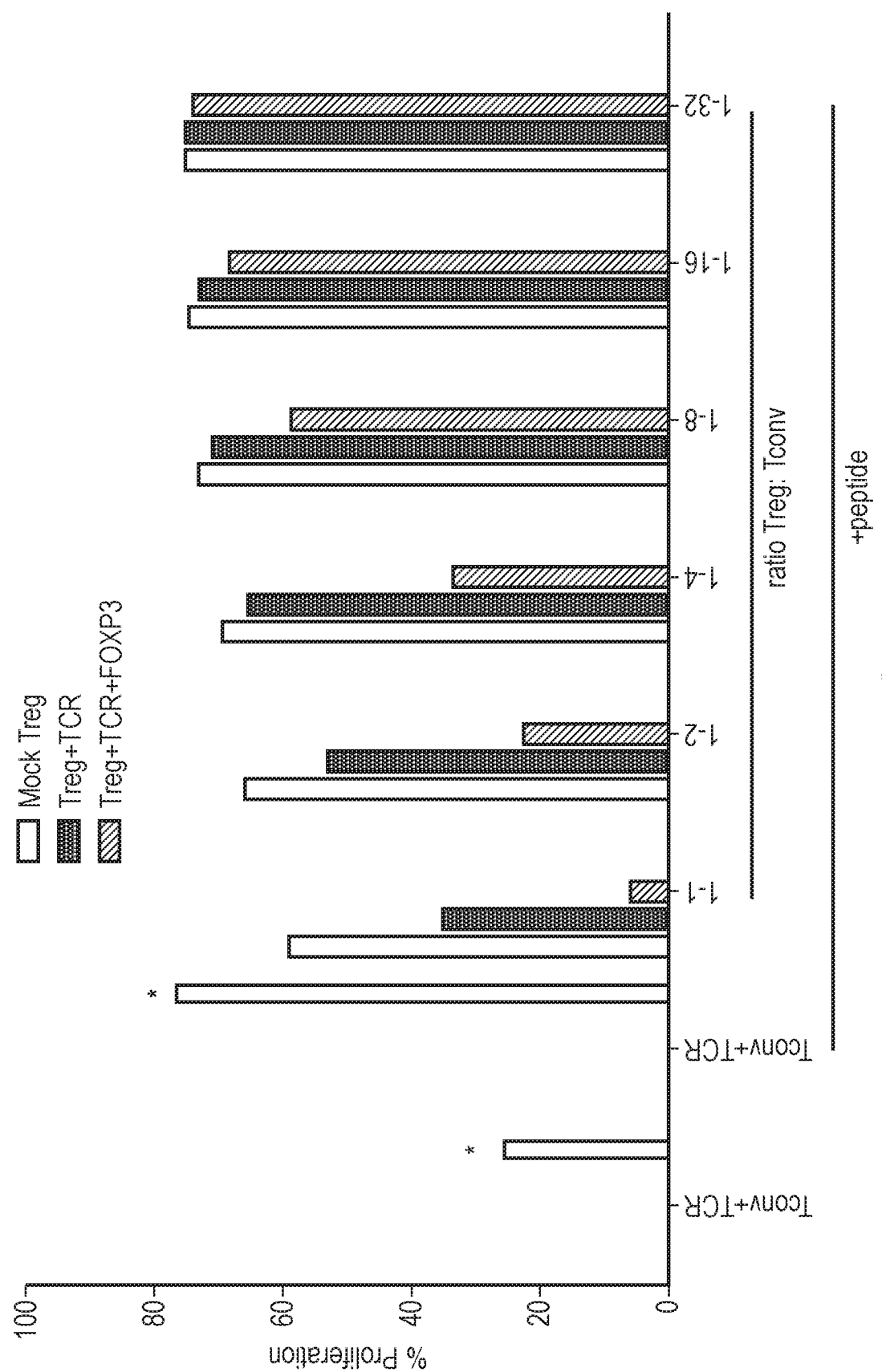
FIG. 1 shows the proliferation of Tconv cells transduced with a TCR construct, with and without peptide (shown with "*"), and the proliferation of the same cells in the presence of mock-transduced Tregs (white bars), Tregs transduced with a TCR construct (black bars) or Tregs transduced with a TCR construct and FOXP3 (grey bars) at different Treg:Tconv ratios.

FIG. 1 shows the proliferation of TCR transduced Tconv cells with and without peptide (blue bars) and the proliferation of the same cells in the presence of Mock Treg (white bars), TCR transduced Treg or TCR+FOXP3 transduced Treg.

On day 4 supernatant was collected and assayed for IL-2 production by ELISA.

Figure 2:
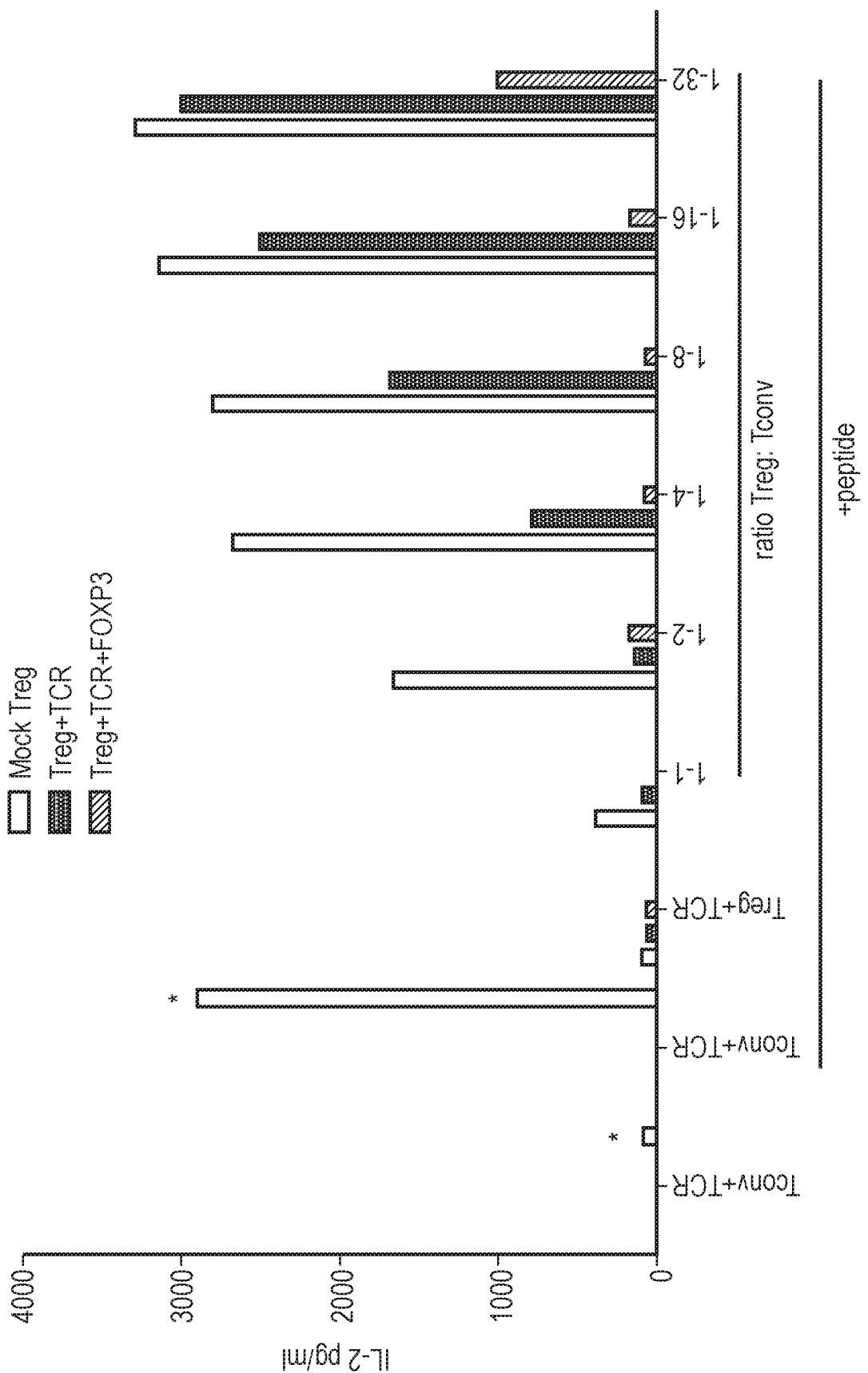
FIG. 2 shows the IL-2 production of Tconv cells transduced with a TCR construct, with and without peptide (shown with "*"), and the IL-2 production of the same cells in the presence of mock-transduced Tregs (white bars), Tregs transduced with a TCR construct (black bars) or Tregs transduced with a TCR construct and FOXP3 (grey bars) at different Treg:Tconv ratios.

FIG. 2 shows the IL-2 production of TCR transduced Tconv cells with and without peptide (blue bars) and the proliferation of the same cells in the presence of Mock Treg (white bars), TCR transduced Treg or TCR+FOXP3 transduced Treg.

Example 2—T Cells from a Different Donor

The experiment described in Example 1 was repeated using T cells from a different donor.

Figure 3:
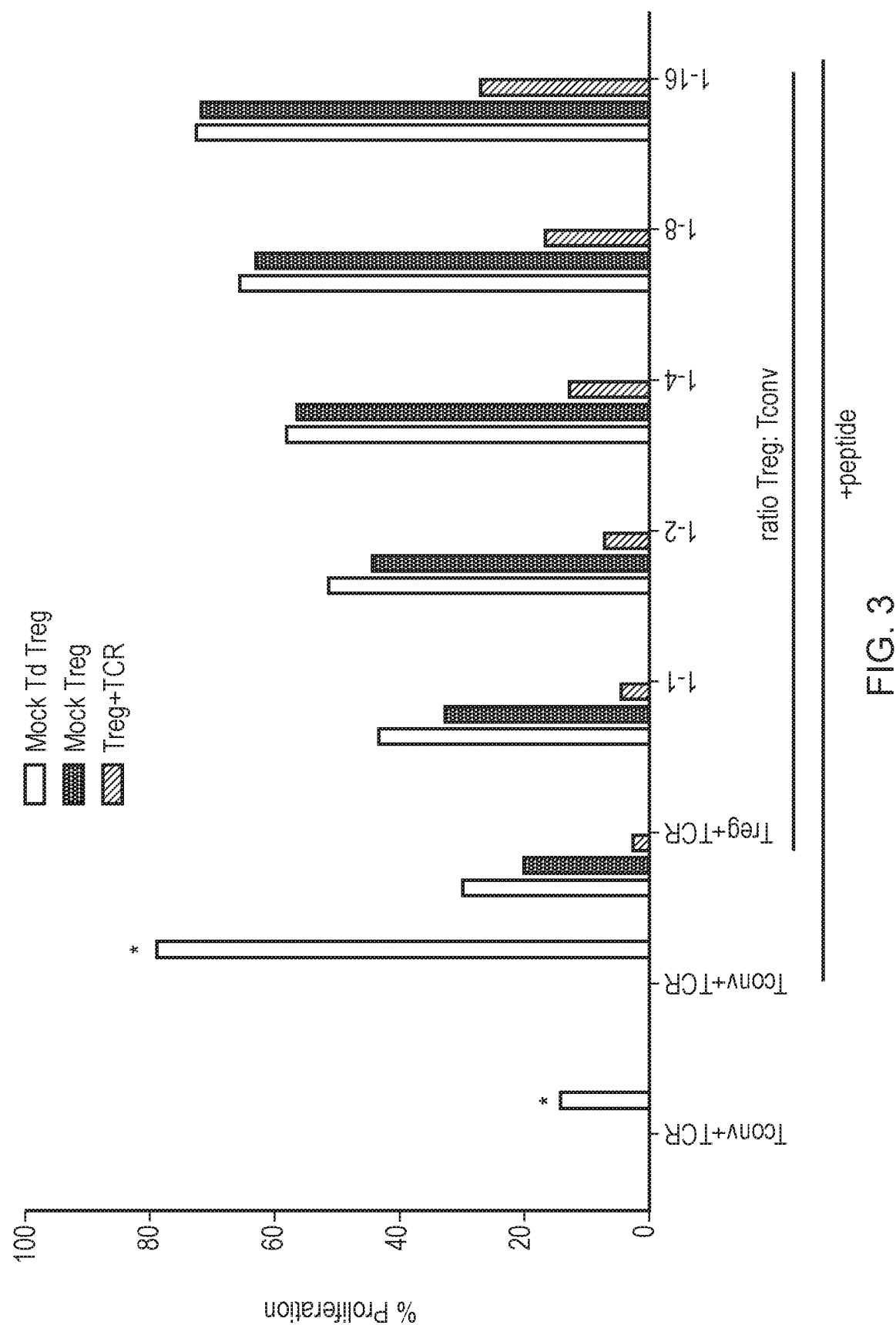
FIG. 3 shows the proliferation of Tconv cells (from a different donor to FIG. 1) transduced with a TCR construct, with and without peptide (shown with "*"), and the proliferation of the same cells in the presence of mock-transduced Tregs (white bars), Tregs transduced with a TCR construct (black bars) or Tregs transduced with a TCR construct and FOXP3 (grey bars) at different Treg:Tconv ratios.

FIG. 3 shows percentage proliferation of TCR transduced T cells.

Figure 4:
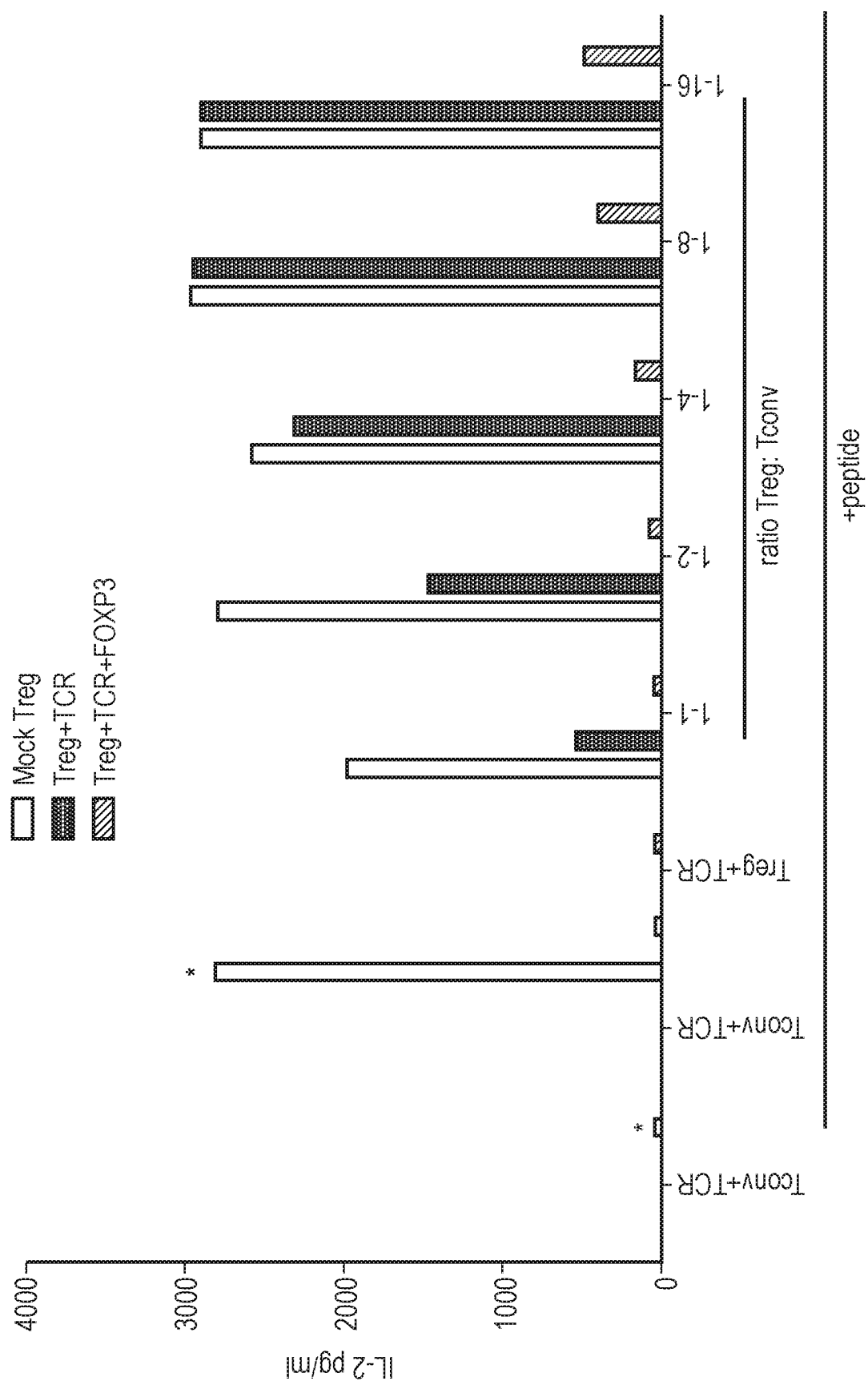
FIG. 4 shows the IL-2 production of Tconv cells (from a different donor to FIG. 2) transduced with a TCR construct with and without peptide (shown with "*") and the proliferation of the same cells in the presence of mock-transduced Tregs (white bars), Tregs transduced with a TCR construct (black bars) or Tregs transduced with a TCR construct and FOXP3 (grey bars) at different Treg:Tconv ratios.

FIG. 4 shows the concentration of IL-2 in supernatants collected from co-culture experiments.

Example 3—Expression of Treg Markers in Transduced Natural Tregs

Mock-transduced Tregs or Tregs transduced with TCR or TCR+FOXP3 were analysed by flow cytometry for the expression of Treg markers (FOXP3, CD25 and CTLA-4) at day 7-10.

Figure 5:
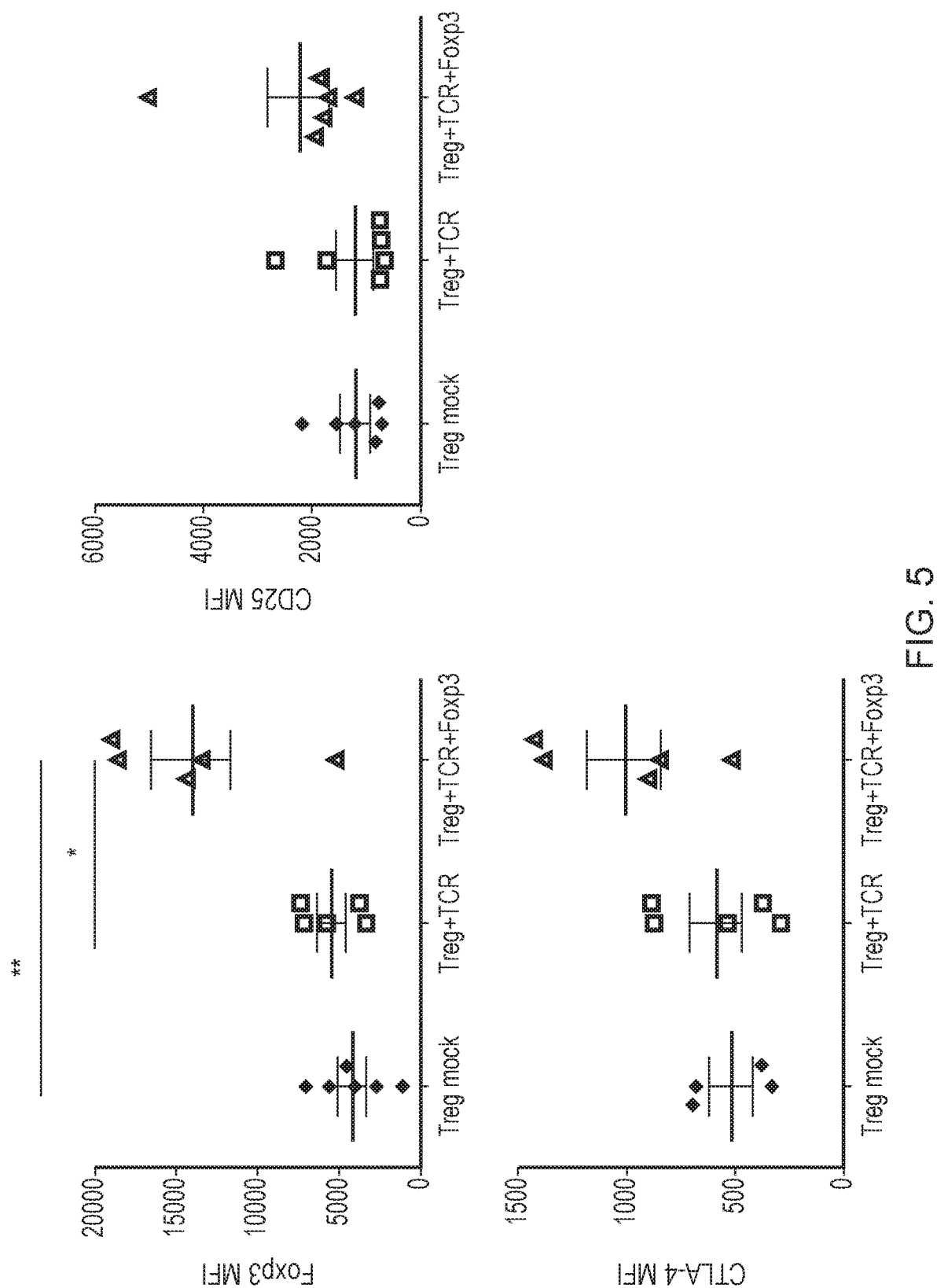
FIG. 5 shows the mean fluorescence intensity (MFI) of Treg markers (FOXP3, CD25 and CTLA-4) in mock-transduced Treg or Treg transduced with TCR or TCR+FOXP3 analysed by flow cytometry at d7-10 after transduction. Dots are representative of individual experiments. 1-way ANOVA was used for statistical analysis $p<0.05*$, $p<0.005**$.

FIG. 5 shows the mean fluorescence intensity (MFI) of each marker. Dots are representative of individual experiments. 1-way ANOVA was used for statistical analysis $p<0.05^*$, $p<0.005^{**}$.

Figure 6:
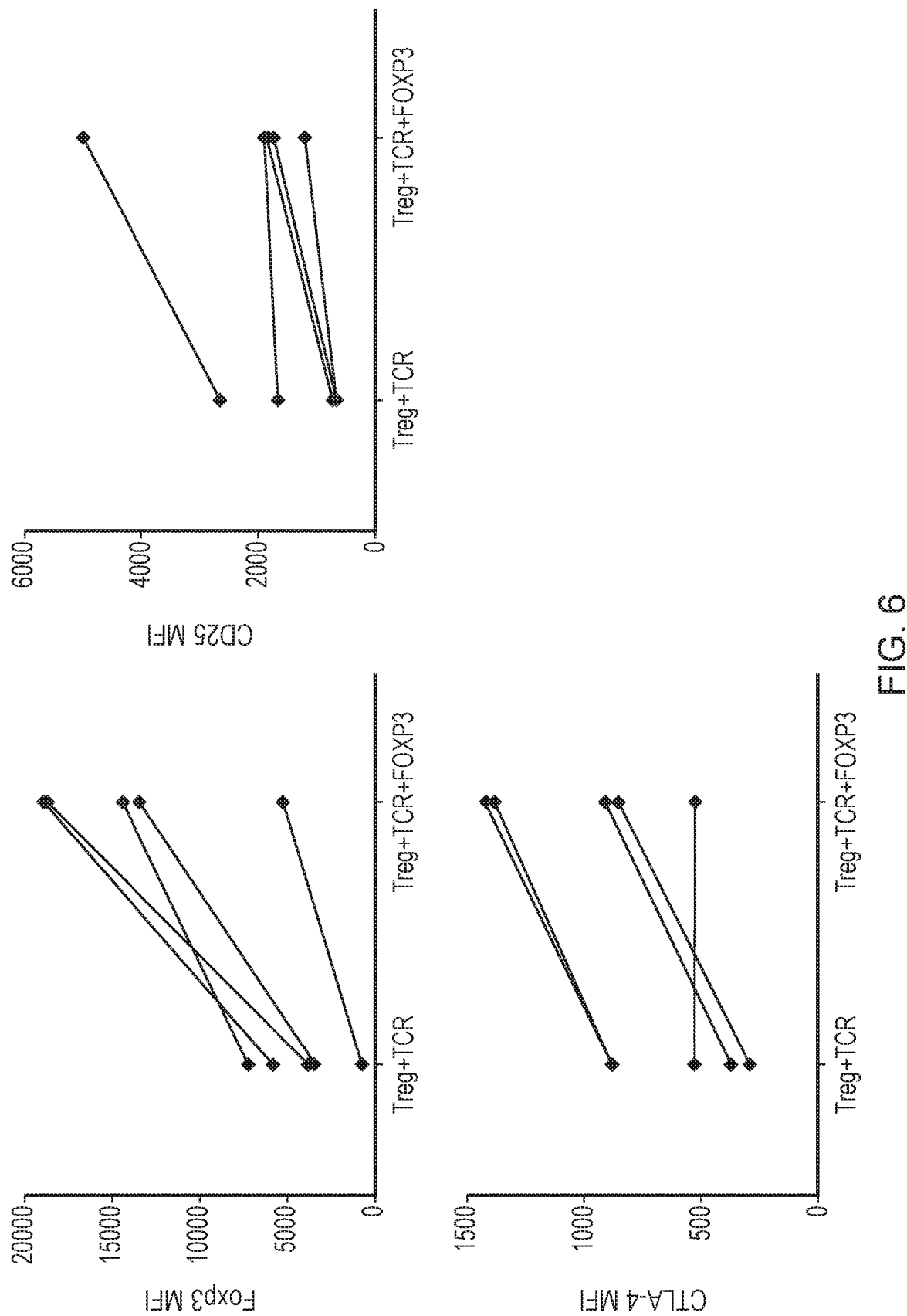
FIG. 6 shows the MFI of FOXP3, CD25 and CTLA-4 in transduced Tregs. Each line represents a single experiment showing MFI of markers on the same Treg transduced with TCR or TCR+FOXP3.

FIG. 6 represents the same data differently. Each line represents a single experiment showing MFI of markers on the same Treg transduced with TCR or TCR+FOXP3.

Example 4—Transduced Natural Tregs Compared to Induced Tregs $CD80^+CD86^+DR4^+$ CHO cells were loaded with peptide and irradiated as described in Example 1C before being re-suspended at $0.1\times10^6$ cells/ml. Transduced responder T cells were stained with CFSE cell trace dye in warmed PBS at 37° C. for 3 minutes before addition of equal volumes of warm FBS and a further 3 minute incubation.

Cells were washed in 5× volume of complete media before being counted and resuspended at $1\times10^6$ transduced cells/ml. The transduction efficiency of Tconv and Treg were determined by flow cytometry. Tregs were removed from culture, washed and resuspended at $1\times10^6$ transduced cells/ml in complete RPMI. Cells were plated 1 Treg:0.1 CHO cells varying parts Tconv. Proliferation was determined by analysing dilution of carboxyfluorescein succinimidyl ester (CFSE)-stained Tconv.

Figure 7:
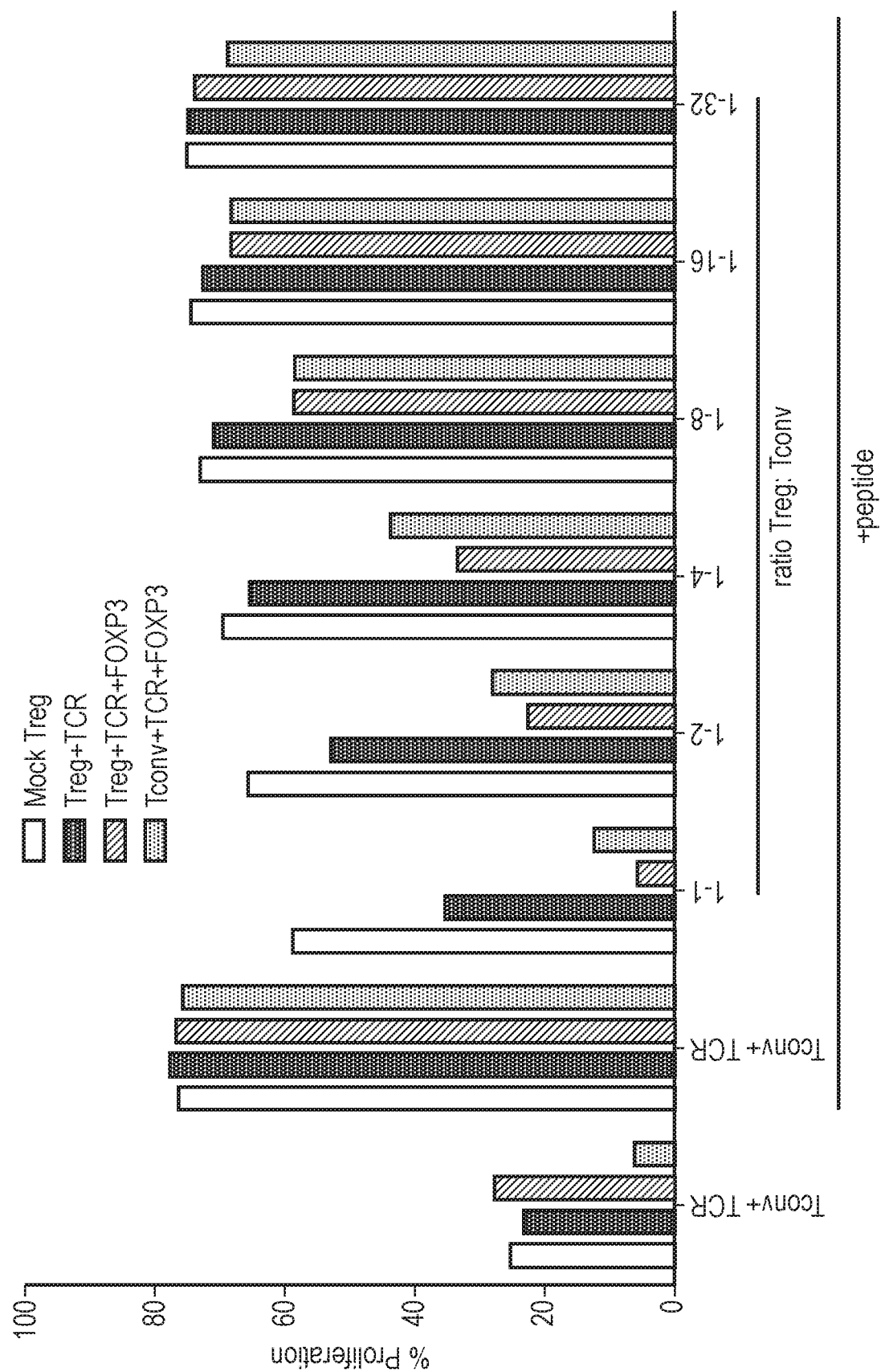
FIG. 7 shows the proliferation of Tconv cells (from a different donor to FIGS. 1 and 3) transduced with a TCR construct, with and without peptide, and the proliferation of the same cells in the presence of mock-transduced Tregs (white bars), Tregs transduced with a TCR construct (black bars), Tregs transduced with a TCR construct and FOXP3 (grey bars) or Tconv cells transduced with a TCR construct and FOXP3, i.e. induced Tregs (red bars, right-hand bar of each data set), at different Treg:Tconv ratios.

The data in FIG. 7 show that TCR+FOXP3-transduced natural Tregs suppress proliferation more effectively than TCR+FOXP3-transduced Tconv cells (i.e. induced Tregs).

Figure 8:
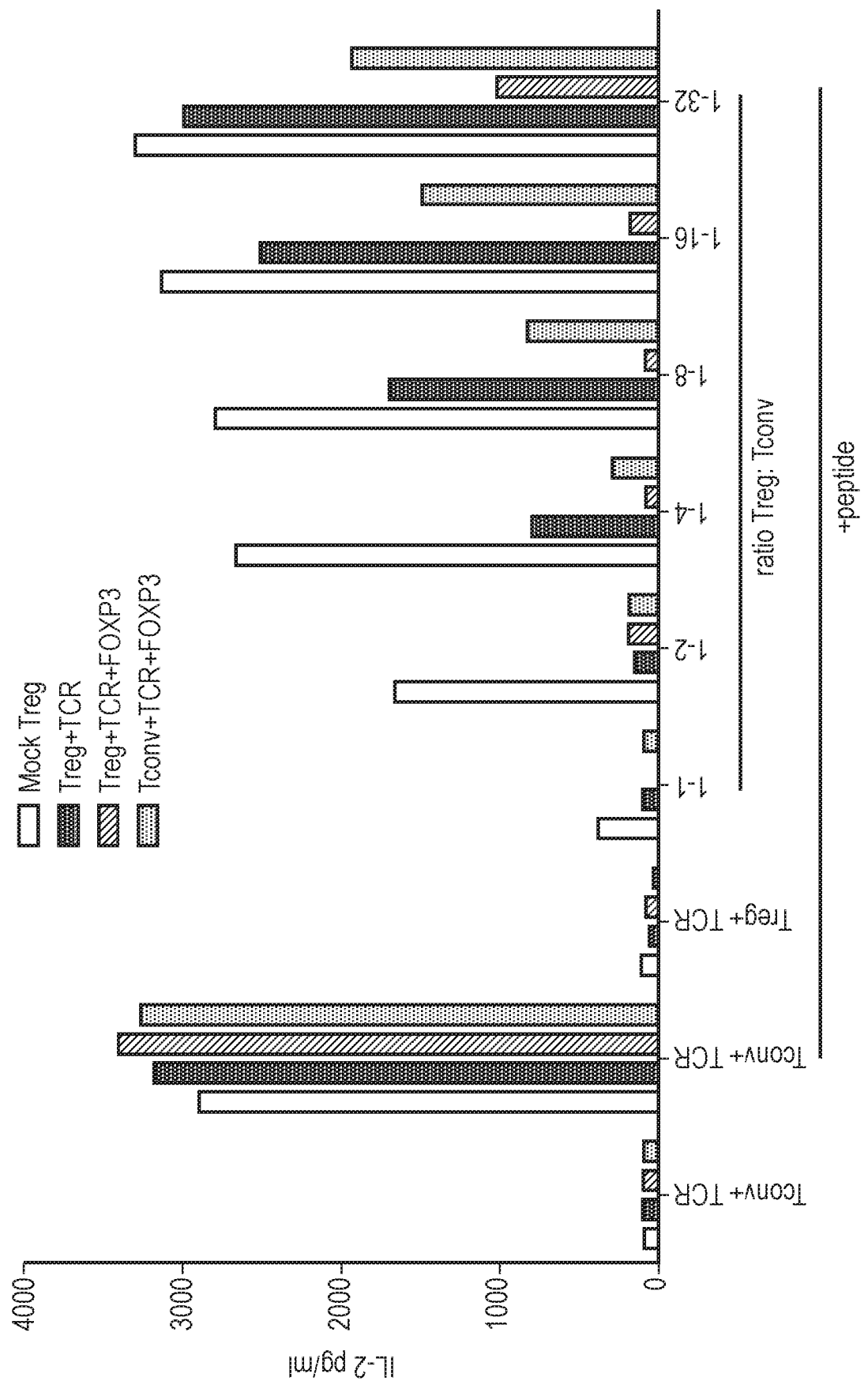
FIG. 8 shows the level of IL-2 production by Tconv cells (from the same donor as FIG. 7) transduced with a TCR construct, with and without peptide, and IL-2 production by the same cells in the presence of mock-transduced Tregs (white bars), Tregs transduced with a TCR construct (black bars), Tregs transduced with a TCR construct and FOXP3 (grey bars) or Tconv transduced with a TCR construct and FOXP3, i.e. induced Tregs (red bars right-hand bar of each data set), at different Treg:Tconv ratios.

Supernatants were collected from the culture media and were assayed for IL-2 by ELISA. The data presented in FIG. 8 show that TCR+FOXP3-transduced natural Tregs suppress IL-2 production more effectively than TCR+FOXP3-transduced Tconv cells (i.e. induced Tregs).

Example 6A—Treg Expressing Exogenous FOXP3 Engraft, Persist and Retain FoxP3, CD25 and TCR Expression Thy1.1+CD4+CD25+ or CD45.1+CD4+CD25+ Treg were isolated from lymph nodes and splenocytes of HLA-DRB*0401 transgenic mice by bead sort. CD45.1+ Treg were transduced with TCR and Thy1.1+ Treg were transduced with TCR+murine FOXP3. 1 day after transduction TCR or TCR+FOXP3 transduced cells were injected in a 1:1 ratio into HLA-DRB*0401 transgenic hosts conditioned with 4Gy irradiation. FACS plots show the ratio of CD45.1:Thy1.1 of injected cells and their respective FOXP3 expression.

After 7 weeks flow cytometry was used to identify engrafted cells by staining for TCR. The ratio of CD45.1:Thy1.1 within the TCR+ population was determined and the phenotype of engrafted CD45.1 (Treg transduced with TCR) or Thy1.1 (Treg transduced with TCR+FOXP3) cells was examined by staining for FOXP3 and CD25.

Figure 9:
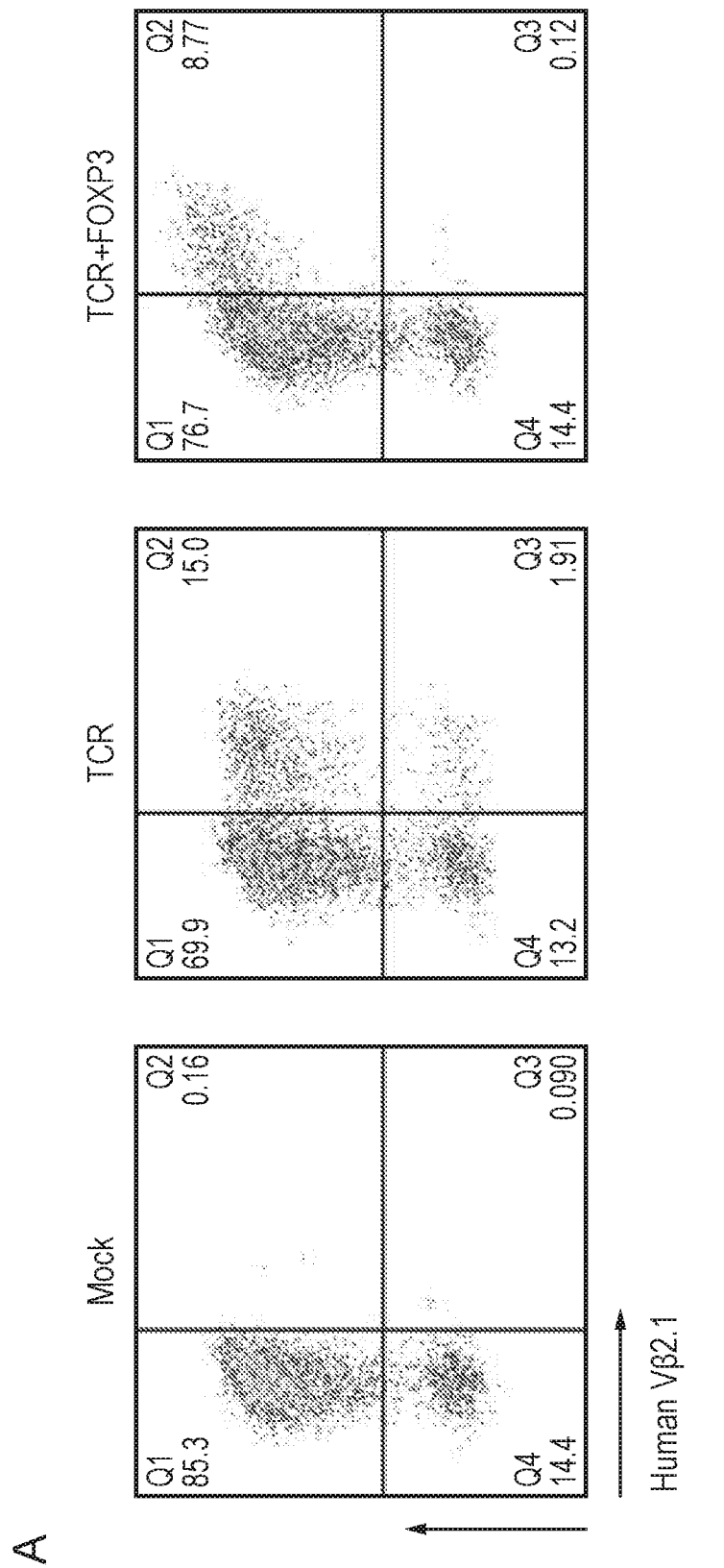
FIG. 9—TCR transduced regulatory T cells can engraft into irradiated hosts but require exogenous FOXP3 expression to prevent accumulation of TCR+FOXP3− cells.
Figure 9:
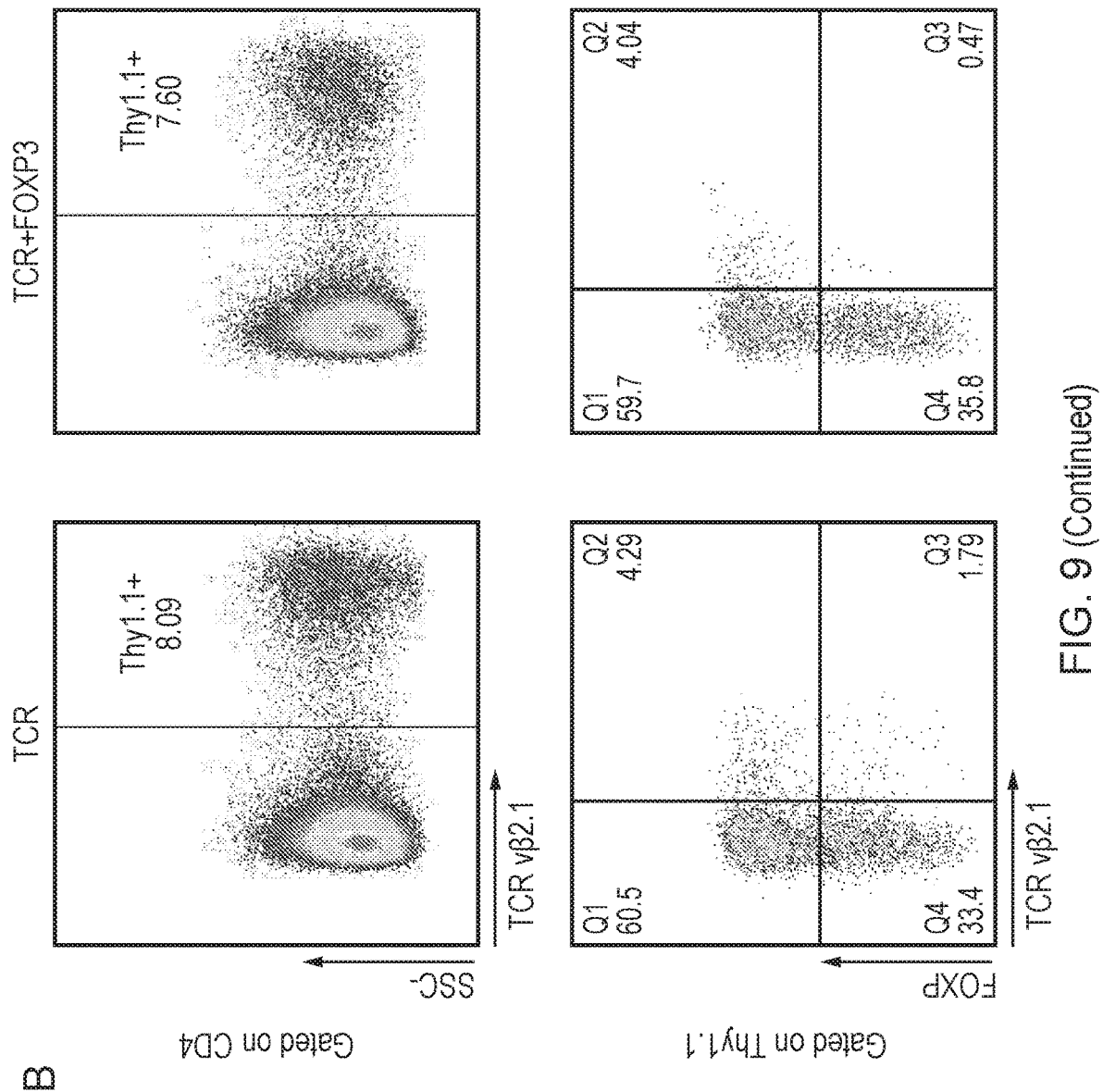
Figure 9:
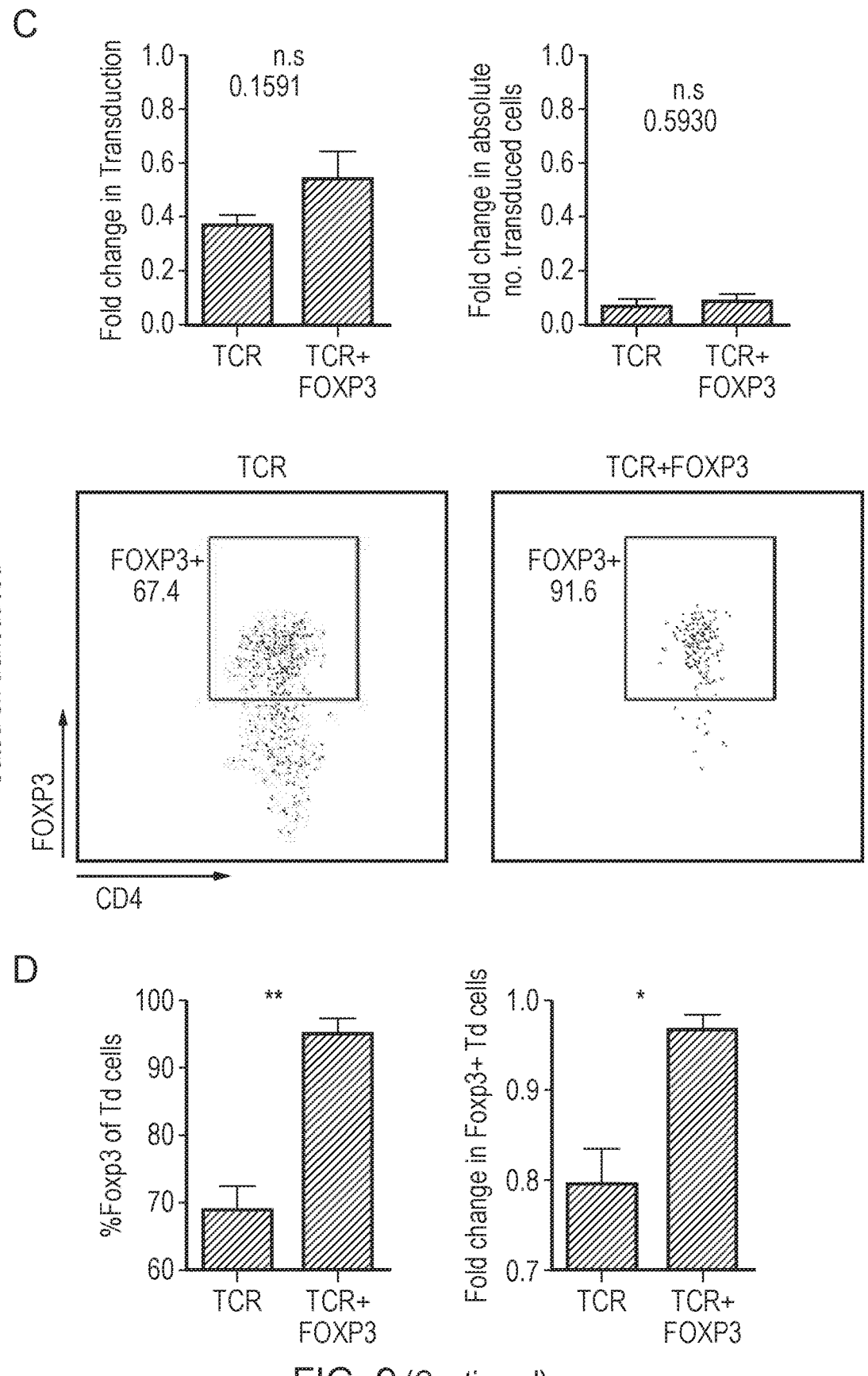

Thy1.1+CD4+CD25+ Treg were isolated from lymph nodes and splenocytes of HLA-DRB*0401 transgenic mice by bead sort. Treg were transduced TCR, TCR+murine FOXP3 or cultured with virus-free supernatant (mock). 1 day after transduction TCR or TCR+FOXP3 transduced cells were injected into HLA-DRB*0401 transgenic hosts conditioned with 4Gy irradiation. 7 weeks later flow cytometry was used to determine the engraftment of transduced Treg FIG. 9, A shows the transduction efficiency determined through expression of human variable 2.1 and murine Foxp3 on d1 post-transduction. FIG. 9, B shows splenocytes from mice that received Treg transduced with TCR or TCR+FOXP3 stained with Thy1.1 to identify transferred cells (top panel) and FOXP3 and TCR (bottom panel). FIG. 9, C shows cumulative data showing fold change in transduction efficiency (left panel) and fold change in absolute number of transduced cells (right panel) relative to day of injection for Treg transduced with TCR or TCR+FOXP3. FIG. 9, D shows a representative expression of FOXP3 within transduced cells 7 weeks after transfer. Graphs show cumulative of percentage FOXP3+ cells within the transduced population at week 7 (left) and the fold change in FOXP3+ cells relative to the day of injection.

Example 6B—Treg Expressing Exogenous FOXP3 Retain Treg Functionality after 7 Weeks In Vivo Whilst Tregs not Expressing Exogenous FOXP3 Acquire the Ability to Produce Effector Cytokines Splenocytes were cultured for 4 hours with CD86+HLA-DR4+CHO cells pulsed with irrelevant peptide or 10 uM MBP. Treg expressing exogenous FOXP3 retain Treg functionality after 7 weeks in vivo as demonstrated by lack of effector cytokine production, whilst Tregs not expressing exogenous FOXP3 acquire the ability to produce effector cytokines (FIG. 10).

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A pharmaceutical composition comprising an engineered regulatory T cell (Treg) with an enhanced ability to suppress immune responses obtained by a process comprising:
   a) isolating a CD4+CD25+CD127−/lowCD45RA+ Treg from a cell population; and
   b) introducing a polynucleotide encoding a FOXP3 polypeptide into the isolated CD4+CD25+CD127−/lowCD45RA+ Treg to enhance the ability of the Treg to suppress immune responses.

2. The pharmaceutical composition according to claim 1, wherein:
   (i) the FOXP3 polypeptide comprises an amino acid sequence which is at least 80% identical to SEQ ID NO: 3 or 4; or
   (ii) the polynucleotide encoding the FOXP3 polypeptide comprises a polynucleotide sequence which is at least 80% identical to SEQ ID NO: 1 or 2.

3. The pharmaceutical composition according to claim 1, wherein the polynucleotide encoding FOXP3 is a contiguous portion of an expression vector.

4. The pharmaceutical composition according to claim 1, wherein the process further comprises introducing a polynucleotide encoding an exogenous T cell receptor (TCR) or a polynucleotide encoding a chimeric antigen receptor (CAR) into the Treg.

5. The pharmaceutical composition according to claim 4, wherein the polynucleotide encoding a FOXP3 polypeptide and the polynucleotide encoding the exogenous TCR or the CAR are provided by a single expression vector.

6. The pharmaceutical composition according to claim 1, wherein the polynucleotide encoding FOXP3 is introduced into the isolated Treg by viral transduction; optionally wherein the polynucleotide encoding FOXP3 is introduced into the isolated Treg by retroviral transduction.

7. The pharmaceutical composition according to claim 1, wherein the cell population comprises or consists of peripheral blood mononuclear cells (PBMCs).

8. The pharmaceutical composition according to claim 1, wherein isolating the Treg comprises
   isolating $CD4^+$ T cells; and
   isolating the $CD4^+CD25^+CD127^-/lowCD45RA^+$ Treg from the $CD4^+$ T cells.

9. The pharmaceutical composition according to claim 1, wherein the isolation of the $CD4^+CD25^+CD127^-/lowCD45RA^+$ Treg comprises selection using immunomagnetic beads or fluorescence-activated cell sorting (FACS).

10. The pharmaceutical composition according to claim 1, wherein the isolated population of Tregs comprises at least 70% $CD4^+CD25^+CD127lowCD45RA^+$ Tregs.

* * * * *

SEQUENCE LISTING

```
<160> NUMBER OF SEQ ID NOS: 7

<210> SEQ ID NO 1
<211> LENGTH: 1296
<212> TYPE: DNA
<213> ORGANISM: Artificial Sequence
<220> FEATURE:
<223> OTHER INFORMATION: FOXP3 polynucleotide sequence

<400> SEQUENCE: 1
atgcccaacc ccaggcctgg caagccctcg gccccttcct tggcccttgg cccatcccca        60
ggagcctcgc ccagctggag ggctgcaccc aaagcctcag acctgctggg ggcccggggc       120 ccaggggaa ccttccaggg ccgagatctt cgaggcgggg cccatgcctc ctcttcttcc       180
ttgaacccca tgccaccatc gcagctgcag ctgcccacac tgccctagt catggtggca       240 ccctccgggg cacggctggg ccccttgccc cacttacagg cactcctcca ggacaggcca       300
catttcatgc accagctctc aacggtggat gcccacgccc ggaccctgt gctgcaggtg       360 cacccctgg agagcccagc catgatcagc ctcacaccac caccaccgc cactgggtc         420 ttctccctca aggcccggcc tggcctccca cctgggatca acgtggccag cctggaatgg       480
gtgtccaggg agccggcact gctctgcacc ttcccaaatc ccagtgcacc caggaaggac       540
agcacccttt cggctgtgcc ccagagctcc tacccactgc tggcaaatgg tgtctgcaag       600
tggcccggat gtgagaaggt cttcgaagag ccagaggact tcctcaagca ctgccaggcg       660
gaccatcttc tggatgagaa gggcagggca caatgtctcc tccagagaga gatggtacag       720
tctctggagc agcagctggt gctggagaag gagaagctga gtgccatgca ggcccacctg       780
gctgggaaaa tggcactgac caaggcttca tctgtggcat catccgacaa gggctcctgc       840
tgcatcgtag ctgctggcag ccaaggccct gtcgtccag cctggtctgg ccccgggag       900 gcccctgaca gcctgtttgc tgtccggagg cacctgtggg gtagccatgg aaacagcaca       960
ttcccagagt tcctccacaa catggactac ttcaagttcc acaacatgcg accccctttc      1020
acctacgcca cgctcatccg ctgggccatc ctggaggctc cagagaagca gcggacactc      1080
```

```
aatgagatct accactggtt cacacgcatg tttgccttct tcagaaacca tcctgccacc    1140
tggaagaacg ccatccgcca caacctgagt ctgcacaagt gctttgtgcg ggtggagagc    1200 gagaagggg ctgtgtggac cgtggatgag ctggagttcc gcaagaaacg gagccagagg    1260
cccagcaggt gttccaaccc tacacctggc ccctga                             1296
```

<210> SEQ ID NO 2
<211> LENGTH: 1352
<212> TYPE: DNA
<213> ORGANISM: Artificial Sequence
<220> FEATURE:
<223> OTHER INFORMATION: FOXP3 polynucleotide sequence

<400> SEQUENCE: 2

```
gaattcgtcg acatgcccaa ccccagaccc ggcaagcctt ctgccccttc tctggccctg      60
ggaccatctc ctggcgcctc cccatcttgg agagccgccc ctaaagccag cgatctgctg     120
ggagctagag gccctggcgg cacattccag ggcagagatc tgagaggcgg agcccacgcc     180
tctagcagca gcctgaatcc catgccccct agccagctgc agctgcctac actgcctctc     240
gtgatggtgg ccctagcgg agctagactg ggccctctgc ctcatctgca ggctctgctg     300
caggaccggc cccactttat gcaccagctg agcaccgtgg acgccacgc agaacacct      360 gtgctgcagg tgcacccct ggaaagccct gccatgatca gcctgacccc tccaaccaca     420
gccaccggcg tgttcagcct gaaggccaga cctggactgc ccctggcat caatgtggcc     480 agcctggaat gggtgtcccg cgaacctgcc ctgctgtgca ccttcccaa tcctagcgcc     540 cccagaaagg acagcacact gtctgccgtg ccccagagca gctatcccct gctggctaac     600
ggcgtgtgca agtggcctgg ctgcgagaag gtgttcgagg aacccgagga cttcctgaag     660
cactgccagg ccgaccatct gctggacgag aaaggcagag cccagtgcct gctgcagcgc     720
gagatggtgc agtccctgga acagcagctg gtgctggaaa agaaaagct gagcgccatg     780 caggcccacc tggccggaaa gatggccctg acaaaagcca gcagcgtggc cagctccgac     840
aagggcagct gttgtatcgt ggccgctggc agccagggac ctgtggtgcc tgcttggagc     900
ggacctagag aggcccccga tagcctgttt gccgtgcgga cacctgtg gggcagccac     960 ggcaactcta ccttccccga gttcctgcac aacatggact acttcaagtt ccacaacatg     1020 aggccccct tcacctacgc caccctgatc agatgggcca ttctggaagc ccccgagaag     1080
cagcggaccc tgaacgagat ctaccactgg tttacccgga tgttcgcctt cttccggaac     1140
caccccgcca cctggaagaa cgccatccgg cacaatctga gcctgcacaa gtgcttcgtg     1200
cgggtggaaa gcgagaaggg cgccgtgtgg acagtggacg agctggaatt cggaagaag     1260 cggtcccaga ggcccagccg tgtagcaat cctacacctg gccctgaggg cagaggaagt     1320
ctgctaacat gcggtgacgt cgaggagaat cc                                  1352
```

<210> SEQ ID NO 3
<211> LENGTH: 431
<212> TYPE: PRT
<213> ORGANISM: Artificial Sequence
<220> FEATURE:
<223> OTHER INFORMATION: FOXP3 polypeptide sequence - UniProtKB
      accession Q9BZS1

<400> SEQUENCE: 3

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
```

```
            20                  25                  30
Ser Asp Leu Leu Gly Ala Arg Gly Pro Gly Thr Phe Gln Gly Arg
            35                  40                  45

Asp Leu Arg Gly Gly Ala His Ala Ser Ser Ser Leu Asn Pro Met
        50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                    85                  90                  95

Gln Asp Arg Pro His Phe Met His Gln Leu Ser Thr Val Asp Ala His
                    100                 105                 110

Ala Arg Thr Pro Val Leu Gln Val His Pro Leu Glu Ser Pro Ala Met
                    115                 120                 125

Ile Ser Leu Thr Pro Pro Thr Ala Thr Gly Val Phe Ser Leu Lys
            130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                    165                 170                 175

Pro Arg Lys Asp Ser Thr Leu Ser Ala Val Pro Gln Ser Ser Tyr Pro
                    180                 185                 190

Leu Leu Ala Asn Gly Val Cys Lys Trp Pro Gly Cys Glu Lys Val Phe
            195                 200                 205

Glu Glu Pro Glu Asp Phe Leu Lys His Cys Gln Ala Asp His Leu Leu
            210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                    245                 250                 255

Gln Ala His Leu Ala Gly Lys Met Ala Leu Thr Lys Ala Ser Ser Val
                    260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
            290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                    325                 330                 335

Arg Pro Pro Phe Thr Tyr Ala Thr Leu Ile Arg Trp Ala Ile Leu Glu
                    340                 345                 350

Ala Pro Glu Lys Gln Arg Thr Leu Asn Glu Ile Tyr His Trp Phe Thr
                    355                 360                 365

Arg Met Phe Ala Phe Phe Arg Asn His Pro Ala Thr Trp Lys Asn Ala
            370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                    405                 410                 415

Arg Ser Gln Arg Pro Ser Arg Cys Ser Asn Pro Thr Pro Gly Pro
                    420                 425                 430

<210> SEQ ID NO 4
```

<211> LENGTH: 441
<212> TYPE: PRT
<213> ORGANISM: Artificial Sequence
<220> FEATURE:
<223> OTHER INFORMATION: FOXP3 polypeptide sequence

<400> SEQUENCE: 4

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Val Glu Leu Ser Ala Met Gln Ala His Leu Ala
                245                 250                 255

Gly Lys Met Ala Leu Thr Lys Ala Ser Ser Val Ala Ser Ser Asp Lys
            260                 265                 270

Gly Ser Cys Cys Ile Val Ala Ala Gly Ser Gln Gly Pro Val Val Pro
        275                 280                 285

Ala Trp Ser Gly Pro Arg Glu Ala Pro Asp Ser Leu Phe Ala Val Arg
    290                 295                 300

Arg His Leu Trp Gly Ser His Gly Asn Ser Thr Phe Pro Glu Phe Leu
305                 310                 315                 320

His Asn Met Asp Tyr Phe Lys Phe His Asn Met Arg Pro Pro Phe Thr
                325                 330                 335

Tyr Ala Thr Leu Ile Arg Trp Ala Ile Leu Glu Ala Pro Glu Lys Gln
            340                 345                 350

Arg Thr Leu Asn Glu Ile Tyr His Trp Phe Thr Arg Met Phe Ala Phe
        355                 360                 365

Phe Arg Asn His Pro Ala Thr Trp Lys Asn Ala Ile Arg His Asn Leu
    370                 375                 380
```

```
Ser Leu His Lys Cys Phe Val Arg Val Glu Ser Glu Lys Gly Ala Val
385                 390                 395                 400

Trp Thr Val Asp Glu Leu Glu Phe Arg Lys Lys Arg Ser Gln Arg Pro
            405                 410                 415

Ser Arg Cys Ser Asn Pro Thr Pro Gly Pro Glu Gly Arg Gly Ser Leu
            420                 425                 430

Leu Thr Cys Gly Asp Val Glu Glu Asn
            435                 440

<210> SEQ ID NO 5
<211> LENGTH: 452
<212> TYPE: PRT
<213> ORGANISM: Artificial Sequence
<220> FEATURE:
<223> OTHER INFORMATION: FOXP3-2A polypeptide sequence

<400> SEQUENCE: 5

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300
```

```
Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro Gly
            420                 425                 430

Ala Thr Asn Phe Ser Leu Leu Lys Gln Ala Gly Asp Val Glu Glu Asn
        435                 440                 445

Pro Gly Pro Ser
    450

<210> SEQ ID NO 6
<211> LENGTH: 462
<212> TYPE: PRT
<213> ORGANISM: Artificial Sequence
<220> FEATURE:
<223> OTHER INFORMATION: FOXP3-2A polypeptide sequence

<400> SEQUENCE: 6

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Ser Leu Asn Pro Met
    50                  55                  60

Pro Pro Ser Gln Leu Gln Leu Pro Thr Leu Pro Leu Val Met Val Ala
65                  70                  75                  80

Pro Ser Gly Ala Arg Leu Gly Pro Leu Pro His Leu Gln Ala Leu Leu
                85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
    195                 200                 205
```

```
Glu Glu Pro Glu Asp Phe Leu Lys His Cys Gln Ala Asp His Leu Leu
        210                 215                 220

Asp Glu Lys Gly Arg Ala Gln Cys Leu Leu Gln Arg Glu Met Val Gln
225                 230                 235                 240

Ser Leu Glu Gln Val Glu Glu Leu Ser Ala Met Gln Ala His Leu Ala
                245                 250                 255

Gly Lys Met Ala Leu Thr Lys Ala Ser Ser Val Ala Ser Ser Asp Lys
            260                 265                 270

Gly Ser Cys Cys Ile Val Ala Ala Gly Ser Gln Gly Pro Val Val Pro
        275                 280                 285

Ala Trp Ser Gly Pro Arg Glu Ala Pro Asp Ser Leu Phe Ala Val Arg
    290                 295                 300

Arg His Leu Trp Gly Ser His Gly Asn Ser Thr Phe Pro Glu Phe Leu
305                 310                 315                 320

His Asn Met Asp Tyr Phe Lys Phe His Asn Met Arg Pro Pro Phe Thr
                325                 330                 335

Tyr Ala Thr Leu Ile Arg Trp Ala Ile Leu Glu Ala Pro Glu Lys Gln
            340                 345                 350

Arg Thr Leu Asn Glu Ile Tyr His Trp Phe Thr Arg Met Phe Ala Phe
        355                 360                 365

Phe Arg Asn His Pro Ala Thr Trp Lys Asn Ala Ile Arg His Asn Leu
    370                 375                 380

Ser Leu His Lys Cys Phe Val Arg Val Glu Ser Lys Gly Ala Val
385                 390                 395                 400

Trp Thr Val Asp Glu Leu Glu Phe Arg Lys Lys Arg Ser Gln Arg Pro
                405                 410                 415

Ser Arg Cys Ser Asn Pro Thr Pro Gly Pro Glu Gly Arg Gly Ser Leu
            420                 425                 430

Leu Thr Cys Gly Asp Val Glu Glu Asn Gly Ala Thr Asn Phe Ser Leu
        435                 440                 445

Leu Lys Gln Ala Gly Asp Val Glu Glu Asn Pro Gly Pro Ser
    450                 455                 460

<210> SEQ ID NO 7
<211> LENGTH: 19
<212> TYPE: PRT
<213> ORGANISM: Artificial Sequence
<220> FEATURE:
<223> OTHER INFORMATION: MBP111-129

<400> SEQUENCE: 7

Leu Ser Arg Phe Ser Trp Gly Ala Glu Gly Gln Arg Pro Gly Phe Gly
1               5                   10                  15

Tyr Gly Gly
```